United States Patent [19]

Sih

[11] 4,243,611
[45] Jan. 6, 1981

[54] 2-DECARBOXY-2-HYDROXYMETHYL-19,20-DIDEHYDRO PG$_2$ COMPOUNDS

[75] Inventor: John C. Sih, Kalamazoo, Mich.

[73] Assignee: The Upjohn Company, Kalamazoo, Mich.

[21] Appl. No.: 26,066

[22] Filed: Apr. 2, 1979

[51] Int. Cl.$^3$ ............................................. C07C 177/00
[52] U.S. Cl. ............................. 568/379; 260/343.3 P;
424/341; 424/343; 260/346.22; 568/838;
556/436; 260/404; 556/465; 556/482;
260/404.5; 564/93; 564/98; 260/408; 564/189;
564/454; 260/410; 260/410.5; 260/410.9 R;
260/413; 542/429; 548/252; 560/53; 560/60;
560/121; 562/463; 562/470; 562/503; 568/646;
568/670; 568/807; 424/769; 424/305; 424/308;
424/317; 424/318; 424/320; 424/321; 424/324;
424/325; 424/330; 424/331; 424/334
[58] Field of Search ...................... 560/121; 562/503;
260/586 R; 568/838

[56] References Cited

U.S. PATENT DOCUMENTS 3,919,285  11/1975  Axen ................................... 560/121
4,064,351  12/1977  Sukai et al. .......................... 560/121

FOREIGN PATENT DOCUMENTS 2635985  2/1978  Fed. Rep. of Germany ............ 560/121

*Primary Examiner*—Robert Gerstl
*Attorney, Agent, or Firm*—Robert A. Armitage; Morris L. Nielsen

[57] ABSTRACT

Prostaglandin derivatives having a 19,20-didehydro, a 19-hydroxy, or a 19-keto feature are disclosed, including processes for preparing them and the appropriate intermediates.

A typical 19-hydroxy compound of this invention is 19-hydroxy-19-methyl-PGF$_{2\alpha}$, methyl ester, represented by the formula

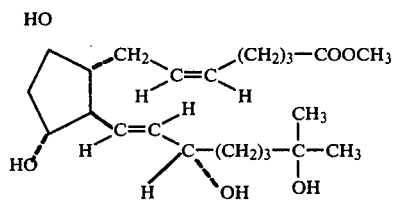

172 Claims, No Drawings

2-DECARBOXY-2-HYDROXYMETHYL-19,20-DIDEHYDRO PG$_2$ COMPOUNDS

The present application incorporates here by reference the entire specification of United States Serial No. 025,899, now Patent No. 4,228,104.

The present invention relates to prostaglandin analogs for which the essential material constituting a disclosure therefor is incorporated by reference here from U.S. Serial No. 025,899, now Patent No. 4,228,104.

DESCRIPTION
BACKGROUND OF THE INVENTION

This invention relates to prostaglandin derivatives and to processes for preparing them.

The prostaglandins are a well-known group of organic compounds, including for example Prostaglandin F$_{2\alpha}$(PGF$_{2\alpha}$) represented by formula I.

The prostaglandins are related to prostanoic acid which has the structure and atom numbering of formula II.

For background on prostaglandins, see for example Bergstrom et al., Pharmacol. Rev. 20, 1 (1968). For nomenclature of the prostaglandins, see N. A. Nelson, J. Medic. Chem. 17, 911 (1974). In the literature, PGF$_{2\alpha}$ may be variously indexed, for example as a derivative of "prosta-5,13-dien-1-oic acid" or "5-heptenoic acid". With respect to "R" and "S" usage, as for the stereochemistry of substituent groups at C-15 herein, see R. S. Cahn, J. Chem. Ed. 41, 116 (1964).

As drawn herein the formulas represent a particular optically active isomer having the same absolute configuration as PGE$_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

Included in the background of chemical literature and patents are the following: K. Green et al., J. Lipid Res. 5, 117 (1969), PGE$_3$ and PGF$_{3\alpha}$, methyl esters; B. Samuelsson, U.S. Pat. No. 3,657,316, 19-hydroxy-PGE$_1$; P. L. Taylor et al., Nature 250, 665 (1974) and FEBS Letters 57, 22 (1975), 19-hydroxy-PGE's and -PGF's; W. Marscheck et al., U.S. Pat. No. 3,878,046, 11-deoxy-19-hydroxy-PGE$_2$; C. J. Sih et al., J. Am. Chem. Soc. 91, 3685 (1969), 19-oxo-PGE$_2$ and -13,14-dihydro-PGE$_1$; J. C. Sih, Prostaglandins 13, 831 (1977), (19R)-19-hydroxy-PGE$_1$,-PGE$_2$,-PGF$_{1\alpha}$, and the title compounds. The (15R) compound, 0.130 g., has R$_f$ 0.35 (TLC on silica gel in acetone-methylene chloride (1:1)), NMR peaks at 5.84–5.29, 4.83–3.05, 2.95–1.96, and 1.17 δ, infrared absorption at 3400, 2950, 1740, 1460, 1370, 1230, 1150, 1070, 970, 900, and 765 cm$^{-1}$, and high resolution mass spectral peak at 643.4037. The (15S) compound, 0.115 g., has R$_f$ 0.26, NMR peaks at 5.82–5.26, 4.92–3.03, 2.93–1.25, and 1.15 δ, and infrared absorption similar to the 15(R) compound.

Following the procedures disclosed herein, but substituting the appropriate starting materials, intermediates, and reagents as are apparent to those skilled in the art, there are prepared the following compounds within the scope of this invention:

I. 19,20-Didehydro($\Delta^{19}$) Prostaglandin-type Compounds of Formula III

A. Wherein R$_1$ is —COOR$_6$ 19,20-didehydro-PGF$_{2\alpha}$, methyl ester,
16,16-dimethyl-19,20-didehydro-PGF$_{2\alpha}$, methyl ester,
16,16-difluoro-19,20-didehydro-PGF$_{2\alpha}$, methyl ester,
(15S)-15-methyl-19,20-didehydro-PGF$_{2\alpha}$, methyl ester,
(15R)-15-methyl-19,20-didehydro-PGF$_{2\alpha}$, methyl ester,
13,14-cis-19,20-didehydro-PGF$_{2\alpha}$, methyl ester,
13,14,19,20-tetradehydro-PGF$_{2\alpha}$, methyl ester,
2,2-difluoro-19,20-didehydro-PGF$_{2\alpha}$, methyl ester,
2,2,16,16-tetrafluoro-19,20-didehydro-PGF$_{2\alpha}$, methyl ester,
2,2-difluoro-(15S)-15-methyl-19,20-didehydro-PGF$_{2\alpha}$, methyl ester,
2,2-difluoro-(15R)-15-methyl-19,20-didehydro-PGF$_{2\alpha}$, methyl ester,
2,2-difluoro-13,14-dihydro-19,20-didehydro-PGF$_{2\alpha}$, methyl ester,
4,5,19,20-tetradehydro-PGF$_{1\alpha}$, methyl ester,
4,5,19,20-tetradehydro-16,16-difluoro-PGF$_{1\alpha}$, methyl ester,
4,5,19,20-tetradehydro-(15S)-15-methyl-PGF$_{1\alpha}$, methyl ester,
4,5,19,20-tetradehydro-(15R)-15-methyl-PGF$_{1\alpha}$, methyl ester,
2,3,19,20-tetradehydro-PGF$_{1\alpha}$, methyl ester,
2,3,19,20-tetradehydro-16,16-difluoro-PGF$_{1\alpha}$, methyl ester,
2,3,19,20-tetradehydro-(15S)-15-methyl-PGF$_{1\alpha}$, methyl ester,
2,3,19,20-tetradehydro-(15R)-15-methyl-PGF$_{1\alpha}$, methyl ester,
2,3,19,20-tetradehydro-13,14-cis-PGF$_{1\alpha}$, methyl ester,
2,3,19,20-tetradehydro-13,14-cis-16,16-dimethyl-PGF$_{1\alpha}$, methyl ester,
2,3,19,20-tetradehydro-13,14-cis-16,16-difluoro-PGF$_{1\alpha}$, methyl ester,
2,3,19,20-tetradehydro-13,14-dihydro-PGF$_{1\alpha}$, methyl ester,
19,20-didehydro-PGF$_{1\alpha}$, methyl ester,
(15S)-15-methyl-19,20-didehydro-PGF$_{1\alpha}$, methyl ester,
(15R)-15-methyl-19,20-didehydro-PGF$_{1\alpha}$, methyl ester,
13,14-cis-19,20-didehydro-PGF$_{1\alpha}$, methyl ester,
13,14-cis-16,16-difluoro-19,20-didehydro-PGF$_{1\alpha}$, methyl ester,
13,14-cis-(15S)-15-methyl-19,20-didehydro-PGF$_{1\alpha}$, methyl ester,
13,14-cis-(15R)-15-methyl-19,20-didehydro-PGF$_{1\alpha}$, methyl ester,
13,14,19,20-tetradehydro-PGF$_{1\alpha}$, methyl ester,
13,14,19,20-tetradehydro-16,16-dimethyl-PGF$_{1\alpha}$, methyl ester,
13,14,19,20-tetradehydro-16,16-difluoro-PGF$_{1\alpha}$, methyl ester,
13,14-dihydro-19,20-didehydro-PGF$_{1\alpha}$, methyl ester,
13,14-dihydro-16,16-dimethyl-19,20-didehydro-PGF$_{1\alpha}$, methyl ester,
13,14-dihydro-16,16-difluoro-19,20-didehydro-PGF$_{1\alpha}$, methyl ester,
13,14-dihydro-(15S)-15-methyl-19,20-didehydro-PGF$_{1\alpha}$, methyl ester,
13,14-dihydro-(15R)-15-methyl-19,20-didehydro-PGF$_{1\alpha}$, methyl ester,
2,2-difluoro-19,20-didehydro-PGF$_{1\alpha}$, methyl ester,
2,2,16,16-tetrafluoro-19,20-didehydro-PGF$_{1\alpha}$, methyl ester,
2,2-difluoro-(15S)-15-methyl-19,20-didehydro-PGF$_{1\alpha}$, methyl ester,
2,2-difluoro-(15R)-15-methyl-19,20-didehydro-PGF$_{1\alpha}$, methyl ester,
2,2-difluoro-13,14-dihydro-19,20-didehydro-PGF$_{1\alpha}$, methyl ester,
3-oxa-19,20-didehydro-PGF$_{1\alpha}$, methyl ester,
3-oxa-16,16-dimethyl-19,20-didehydro-PGF$_{1\alpha}$, methyl ester,
3-oxa-13,14-cis-19,20-didehydro-PGF$_{1\alpha}$, methyl ester,
3-oxa-13,14,19,20-tetradehydro-PGF$_{1\alpha}$, methyl ester,
3-oxa-13,14-dihydro-19,20-didehydro-PGF$_{1\alpha}$, methyl ester,
5-oxa-19,20-didehydro-PGF$_{1\alpha}$, methyl ester,
5-oxa-16,16-dimethyl-19,20-didehydro-PGF$_{1\alpha}$, methyl ester,
5-oxa-13,14-cis-19,20-didehydro-PGF$_{1\alpha}$, methyl ester,
5-oxa-13,14,19,20-tetradehydro-PGF$_{1\alpha}$, methyl ester, 5-oxa-13,14-dihydro-19,20-didehydro-PGF$_{1\alpha}$, methyl ester,
3-oxa-3,7-inter-m-phenylene-4,5,6-trinor-19,20-didehydro-PGF$_{1\alpha}$, methyl ester,
3-oxa-3,7-inter-m-phenylene-4,5,6-trinor-16,16-dimethyl-19,20-didehydro-PGF$_{1\alpha}$, methyl ester,
3-oxa-3,7-inter-m-phenylene-4,5,6-trinor-16,16-difluoro-19,20-didehydro-PGF$_{1\alpha}$, methyl ester,
3-oxa-3,7-inter-m-phenylene-4,5,6-trinor-(15S)-15-methyl-19,20-didehydro-PGF$_{1\alpha}$, methyl ester,
3-oxa-3,7-inter-m-phenylene-4,5,6-trinor-(15R)-15-methyl-19,20-didehydro-PGF$_{1\alpha}$, methyl ester,
3-oxa-3,7-inter-m-phenylene-4,5,6-trinor-13,14,19,20-tetradehydro-PGF$_{1\alpha}$, methyl ester,
3-oxa-3,7-inter-m-phenylene-4,5,6-trinor-16,16-difluoro-13,14,19,20-tetradehydro-PGF$_{1\alpha}$, methyl ester,
11-deoxy-19,20-didehydro-PGF$_{2\alpha}$, methyl ester,
11-deoxy-16,16-dimethyl-19,20-didehydro-PGF$_{2\alpha}$, methyl ester,
11-deoxy-16,16-difluoro-19,20-didehydro-PGF$_{2\alpha}$, methyl ester,
11-deoxy-(15S)-15-methyl-19,20-didehydro-PGF$_{2\alpha}$, methyl ester,
11-deoxy-(15R)-15-methyl-19,20-didehydro-PGF$_{2\alpha}$, methyl ester,
11-deoxy-13,14-cis-19,20-didehydro-PGF$_{2\alpha}$, methyl ester,
11-deoxy-13,14,19,20-tetradehydro-PGF$_{2\alpha}$, methyl ester,
11-deoxy-2,2-difluoro-19,20-didehydro-PGF$_{2\alpha}$, methyl ester,
11-deoxy-2,2,16,16-tetrafluoro-19,20-didehydro-PGF$_{2\alpha}$, methyl ester,
11-deoxy-2,2-difluoro-(15S)-15-methyl-19,20-didehydro-PGF$_{2\alpha}$, methyl ester,
11-deoxy-2,2-difluoro-(15R)-methyl-19,20-didehydro-PGF$_{2\alpha}$, methyl ester,
11-deoxy-2,2-difluoro-19,20-didehydro-PGF$_{1\alpha}$, methyl ester,
11-deoxy-4,5,19,20-tetradehydro-PGF$_{1\alpha}$, methyl ester,
11-deoxy-4,5,19,20-tetradehydro-16,16-difluoro-PGF$_{1\alpha}$, methyl ester,
11-deoxy-(15S)-15-methyl-4,5,19,20-tetradehydro-PGF$_{1\alpha}$, methyl ester,
11-deoxy-(15R)-15-methyl-4,5,19,20-tetradehydro-PGF$_{1\alpha}$, methyl ester,
11-deoxy-2,3,19,20-tetradehydro-PGF$_{1\alpha}$, methyl ester,
11-deoxy-2,3,19,20-tetradehydro-16,16-difluoro-PGF$_{1\alpha}$, methyl ester,
11-deoxy-2,3,19,20-tetradehydro-(15S)-15-methyl-PGF$_{1\alpha}$, methyl ester,
11-deoxy-2,3,19,20-tetradehydro-(15R)-15-methyl-PGF$_{1\alpha}$, methyl ester,
11-deoxy-2,3,19,20-tetradehydro-13,14-cis-PGF$_{1\alpha}$, methyl ester,
11-deoxy-2,3,19,20-tetradehydro-13,14-cis-16,16-dimethyl-PGF$_{1\alpha}$, methyl ester,
11-deoxy-2,3,19,20-tetradehydro-13,14-cis-16,16-difluoro-PGF$_{1\alpha}$, methyl ester,
11-deoxy-2,3,19,20-tetradehydro-13,14-dihydro-PGF$_{1\alpha}$, methyl ester,
11-deoxy-19,20-didehydro-PGF$_{1\alpha}$, methyl ester,
11-deoxy-(15S)-15-methyl-19,20-didehydro-PGF$_{1\alpha}$, methyl ester,
11-deoxy-(15R)-15-methyl-19,20-didehydro-PGF$_{1\alpha}$, methyl ester,
11-deoxy-13,14-cis-19,20-didehydro-PGF$_{1\alpha}$, methyl ester,
11-deoxy-13,14-cis-16,16-difluoro-19,20-didehydro-PGF$_{1\alpha}$, methyl ester,
11-deoxy-13,14-cis-(15S)-15-methyl-19,20-didehydro-PGF$_{1\alpha}$, methyl ester,
11-deoxy-13,14-cis-(15R)-15-methyl-19,20-didehydro-PGF$_{1\alpha}$, methyl ester,
11-deoxy-13,14,19,20-tetradehydro-PGF$_{1\alpha}$, methyl ester,
11-deoxy-13,14,19,20-tetradehydro-16,16-dimethyl-PGF$_{1\alpha}$, methyl ester,
11-deoxy-11$\alpha$-hydroxymethyl-19,20-didehydro-PGF$_{2\alpha}$, methyl ester,
11-deoxy-11$\alpha$-hydroxymethyl-16,16-dimethyl-19,20-didehydro-PGF$_{2\alpha}$, methyl ester,
11-deoxy-11$\alpha$-hydroxymethyl-16,16-difluoro-19,20-didehydro-PGF$_{2\alpha}$, methyl ester,
11-deoxy-11$\alpha$-hydroxymethyl-(15S)-15-methyl-19,20-didehydro-PGF$_{2\alpha}$, methyl ester,
11-deoxy-11$\alpha$-hydroxymethyl-(15R)-15-methyl-19,20-didehydro-PGF$_{2\alpha}$, methyl ester,
11-deoxy-11$\alpha$-hydroxymethyl-13,14-cis-19,20-didehydro-PGF$_{2\alpha}$, methyl ester,
11-deoxy-11$\alpha$-hydroxymethyl-13,14,19,20-tetradehydro-PGF$_{2\alpha}$, methyl ester,
11-deoxy-11$\alpha$-hydroxymethyl-2,2-difluoro-19,20-didehydro-PGF$_{2\alpha}$, methyl ester,
11-deoxy-11$\alpha$-hydroxymethyl-2,2,16,16-tetrafluoro-19,20-didehydro-PGF$_{2\alpha}$, methyl ester,
11-deoxy-11$\alpha$-hydroxymethyl-2,2-difluoro-(15S)-15-methyl-19,20-didehydro-PGF$_{2\alpha}$, methyl ester,
11-deoxy-11$\alpha$-hydroxymethyl-2,2-difluoro-(15R)-15-methyl-19,20-didehydro-PGF$_{2\alpha}$, methyl ester,
11-deoxy-11$\alpha$-hydroxymethyl-2,2-difluoro-19,20-didehydro-PGF$_{2\alpha}$, methyl ester,
11-deoxy-11$\alpha$-hydroxymethyl-4,5,19,20-tetradehydro-PGF$_{1\alpha}$, methyl ester,
11-deoxy-11$\alpha$-hydroxymethyl-4,5,19,20-tetradehydro-16,16-difluoro-PGF$_{1\alpha}$, methyl ester,
11-deoxy-11$\alpha$-hydroxymethyl-(15S)-15-methyl-4,5,19,20-tetradehydro-PGF$_{1\alpha}$, methyl ester,
11-deoxy-11$\alpha$-hydroxymethyl-(15R)-15-methyl-4,5,19,20-tetradehydro-PGF$_{1\alpha}$, methyl ester,
11-deoxy-11$\alpha$-hydroxymethyl-2,3,19,20-tetrahydro-PGF$_{1\alpha}$, methyl ester, Likewise following the procedures disclosed herein, there are prepared the corresponding 19,20-didehydro-PGF$_\beta$, -PGE, and -9-deoxy-9-methylene-PGE methyl ester compounds within the scope of formula III.

Also following the procedures disclosed herein, there are prepared the corresponding free acid from each of the above methyl esters and, likewise, the corresponding sodium salt.

B. Wherein R$_1$ is —CH$_2$OH.
2-decarboxy-2-hydroxymethyl-19,20-didehydro-PGF$_{2\alpha}$,
2-decarboxy-2-hydroxymethyl-4,5,19,20-tetradehydro-PGF$_{1\alpha}$,
2-decarboxy-2-hydroxymethyl-(15S)-15-methyl-4,5,19,20-tetradehydro-PGF$_{1\alpha}$,
2-decarboxy-2-hydroxymethyl-(15R)-15-methyl-4,5,19,20-tetradehydro-PGF$_{1\alpha}$,
2-decarboxy-2-hydroxymethyl-4,5,13,14,19,20-hexadehydro-PGF$_{1\alpha}$,
2-decarboxy-2-hydroxymethyl-4,5,13,14,19,20-hexadehydro-16,16-difluoro-PGF$_{1\alpha}$,
2-decarboxy-2-hydroxymethyl-2,3,19,20-tetradehydro-PGF$_{1\alpha}$,
2-decarboxy-2-hydroxymethyl-2,3,19,20-tetradehydro-16,16-difluoro-PGF$_{1\alpha}$,
2-decarboxy-2-hydroxymethyl-2,3,19,20-tetradehydro-15(S)-15-methyl-PGF$_{1\alpha}$, 2-decarboxy-2-hydroxymethyl-2,3,19,20-tetradehydro-15(R)-15-methyl-PGF$_{1\alpha}$,
2-decarboxy-2-hydroxymethyl-19,20-didehydro-PGF$_{1\alpha}$,
2-decarboxy-2-hydroxymethyl-16,16-dimethyl-19,20-didehydro-PGF$_{1\alpha}$,
2-decarboxy-2-hydroxymethyl-16,16-difluoro-19,20-didehydro-PGF$_{1\alpha}$,
2-decarboxy-2-hydroxymethyl-13,14-dihydro-19,20-didehydro-PGF$_{1\alpha}$,
2-decarboxy-2-hydroxymethyl-11-deoxy-19,20-didehydro-PGF$_{2\alpha}$,
2-decarboxy-2-hydroxymethyl-11-deoxy-4,5,19,20-tetradehydro-PGF$_{1\alpha}$,
2-decarboxy-2-hydroxymethyl-11-deoxy-(15S)-15-methyl-4,5,19,20-tetradehydro-PGF$_{1\alpha}$,
2-decarboxy-2-hydroxymethyl-11-deoxy-(15R)-15-methyl-4,5,19,20-tetradehydro-PGF$_{1\alpha}$,
2-decarboxy-2-hydroxymethyl-11-deoxy-4,5,13,14,19,20-hexadehydro-PGF$_{1\alpha}$,
2-decarboxy-2-hydroxymethyl-11-deoxy-4,5,13,14,19,20-hexadehydro-16,16-difluoro-PGF$_{1\alpha}$,
2-decarboxy-2-hydroxymethyl-11-deoxy-2,3,19,20-tetradehydro-PGF$_{1\alpha}$,
2-decarboxy-2-hydroxymethyl-11-deoxy-2,3,19,20-tetradehydro-16,16-difluoro-PGF$_{1\alpha}$,
2-decarboxy-2-hydroxymethyl-11-deoxy-2,3,19,20-tetradehydro-(15R)-15-methyl-PGF$_{1\alpha}$,
2-decarboxy-2-hydroxymethyl-11-deoxy-2,3,19,20-tetradehydro-(15S)-15-methyl-PGF$_{1\alpha}$,
2-decarboxy-2-hydroxymethyl-11-deoxy-19,20-didehydro-PGF$_{1\alpha}$,
2-decarboxy-2-hydroxymethyl-11-deoxy-16,16-dimethyl-19,20-didehydro-PGF$_{1\alpha}$,
2-decarboxy-2-hydroxymethyl-11-deoxy-16,16-difluoro-19,20-didehydro-PGF$_{1\alpha}$,
2-decarboxy-2-hydroxymethyl-11-deoxy-13,14-dihydro-19,20-didehydro-PGF$_{1\alpha}$,
2-decarboxy-2-hydroxymethyl-11-deoxy-11α-hydroxymethyl-19,20-didehydro-PGF$_{2\alpha}$,
2-decarboxy-2-hydroxymethyl-11-deoxy-11α-hydroxymethyl-4,5,19,20-tetradehydro-PGF$_{1\alpha}$,
2-decarboxy-2-hydroxymethyl-11-deoxy-11α-hydroxymethyl-(15S)-15-methyl-4,5,19,20-tetradehydro-PGF$_1$,
2-decarboxy-2-hydroxymethyl-11-deoxy-11α-hydroxymethyl-(15R)-15-methyl-4,5,19,20-tetradehydro-PGF$_{1\alpha}$,
2-decarboxy-2-hydroxymethyl-11-deoxy-11α-hydroxymethyl-4,5,13,14,19,20-hexadehydro-PGF$_{1\alpha}$,
2-decarboxy-2-hydroxymethyl-11-deoxy-11α-hydroxymethyl-4,5,13,14,19,20-hexadehydro-16,16-difluoro-PGF$_{1\alpha}$,
2-decarboxy-2-hydroxymethyl-11-deoxy-11α-hydroxymethyl-2,3,19,20-tetradehydro-PGF$_{1\alpha}$,
2-decarboxy-2-hydroxymethyl-11-deoxy-11α-hydroxymethyl-2,3,19,20-tetradehydro-16,16-difluoro-PGF$_{1\alpha}$,
2-decarboxy-2-hydroxymethyl-11-deoxy-11α-hydroxymethyl-2,3,19,20-tetradehydro-(15S)-15-methyl-PGF$_{1\alpha}$,
2-decarboxy-2-hydroxymethyl-11-deoxy-11α-hydroxymethyl-2,3,19,20-tetradehydro-(15R)-15-methyl-PGF$_{1\alpha}$,
2-decarboxy-2-hydroxymethyl-11-deoxy-11α-hydroxymethyl-19,20-didehydro-PGF$_{1\alpha}$,
2-decarboxy-2-hydroxymethyl-11-deoxy-11α-hydroxymethyl-16,16-dimethyl-19,20-didehydro-PGF$_{1\alpha}$, Likewise following the procedures disclosed herein, there are prepared the corresponding 19,20-didehydro-PGF$_\beta$, -PGE, and 9-deoxo-9-methylene-PGE 2-decarboxy-2-hydroxymethyl compounds within the scope of formula III.

C. Wherein R$_1$ is —CH$_2$NH$_2$ 2-decarboxy-2-amino-19,20-didehydro-PGF$_{2\alpha}$,
2-decarboxy-2-amino-(15S)-15-methyl-19,20-didehydro-PGF$_{2\alpha}$,
2-decarboxy-2-amino-(15)-15-methyl-19,20-didehydro-PGF$_{2\alpha}$,
2-decarboxy-2-amino-2,3,19,20-tetradehydro-PGF$_{1\alpha}$,
2-decarboxy-2-amino-2,3,19,20-tetradehydro-16,16-dimethyl-PGF$_{1\alpha}$,
2-decarboxy-2-amino-2,3,19,20-tetradehydro-16,16-difluoro-PGF$_{1\alpha}$,
2-decarboxy-2amino-19,20-didehydro-PGF$_{1\alpha}$,
2-decarboxy-2-amino-16,16-dimethyl-19,20-didehydro-PGF$_{1\alpha}$,
2-decarboxy-2-amino-16,16-difluoro-19,20-didehydro-PGF$_{1\alpha}$,
2-decarboxy-2-amino-11-deoxy-19,20-didehydro-PGF$_{1\alpha}$,
2-decarboxy-2-amino-11-deoxy-(15S)-15-methyl-19,20-didehydro-PGF$_{2\alpha}$,
2-decarboxy-2-amino-11-deoxy-(15R)-15-methyl-19,20-didehydro-PGF$_{2\alpha}$,
2-decarboxy-2-amino-11-deoxy-2,3,19,20-tetradehydro-PGF$_{1\alpha}$,
2-decarboxy-2-amino-11-deoxy-2,3,19,20-tetradehydro-16,16-dimethyl-PGF$_{1\alpha}$,
2-decarboxy-2-amino-11-deoxy-2,3,19,20-tetradehydro-16,16-difluoro-PGF$_{1\alpha}$,
2-decarboxy-2-amino-11-deoxy-19,20-didehydro-PGF$_{1\alpha}$,
2-decarboxy-2-amino-11-deoxy-16,16-dimethyl-19,20-didehydro-PGF$_{1\alpha}$,
2-decarboxy-2-amino-11-deoxy-16,16-difluoro-19,20-didehydro-PGF$_{1\alpha}$,
2-decarboxy-2-amino-11-deoxy-11α-hydroxymethyl-19,20-didehydro-PGF$_{2\alpha}$,
2-decarboxy-2-amino-11-deoxy-11α-hydroxymethyl-(15S)-15-methyl-19,20-didehydro-PGF$_{2\alpha}$,
2-decarboxy-2-amino-11-deoxy-11α-hydroxymethyl-(15R)-15-methyl-19,20-didehydro-PGF$_{2\alpha}$,
2-decarboxy-2-amino-11-deoxy-11α-hydroxymethyl-2,3,19,20-tetradehydro-PGF$_{1\alpha}$,
2-decarboxy-2-amino-11-deoxy-11α-hydroxymethyl-2,3,19,20-tetradehydro-16,16-dimethyl-PGF$_{1\alpha}$,
2-decarboxy-2-amino-11-deoxy-11α-hydroxymethyl-2,3,19,20-tetradehydro-16,16-difluoro-PGF$_{1\alpha}$,
2-decarboxy-2-amino-11-deoxy-11α-hydroxymethyl-19,20-didehydro-PGF$_{1\alpha}$,
2-decarboxy-2-amino-11-deoxy-11α-hydroxymethyl-16,16-dimethyl-19,20-didehydro-PGF$_{1\alpha}$,
2-decarboxy-2-amino-11-deoxy-11α-hydroxymethyl-16,16-difluoro-19,20-didehydro-PGF$_{1\alpha}$.

Likewise following the procedures disclosed herein, there are prepared the corresponding 19,20-didehydro-PGF$_{1\beta}$, ePGE$_1$, and 9-deoxo-9-methylene-PGE 2-decarboxy-2-amino compounds within the scope of formula III wherein R$_1$ is —CH$_2$NH$_2$.

D. Wherein R$_1$ is —C(O)—NH$_2$ 19,20-didehydro-PGF$_{2\alpha}$, amide,
2,2-difluoro-19,20-didehydro-PGF$_{2\alpha}$, amide,
4,5,19,20-tetradehydro-PGF$_{1\alpha}$, amide,
4,5,19,20-tetradehydro-(15S)-15-methyl-PGF$_{1\alpha}$, amide, 4,5,19,20-tetradehydro-(15R)-15-methyl-PGF$_{1\alpha}$, amide,
2,3,19,20-tetradehydro-PGF$_{1\alpha}$, amide,
2,3,19,20-tetradehydro-16,16-dimethyl-PGF$_{1\alpha}$, amide,
2,3,19,20-tetradehydro-16,16-difluoro-PGF$_{1\alpha}$, amide,
19,20-didehydro-PGF$_{1\alpha}$, amide,
16,16-dimethyl-19,20-didehydro-PGF$_{1\alpha}$, amide,
16,16-difluoro-19,20-didehydro-PGF$_{1\alpha}$, amide,
2,2-difluoro-19,20-didehydro-PGF$_{1\alpha}$, amide,
3-oxa-3,7-inter-m-phenylene-4,5,6-trinor-19,20-didehydro-PGF$_{1\alpha}$, amide,
3-oxa-3,7-inter-m-phenylene-4,5,6-trinor-(15S)-15-methyl-19,20-didehydro-PGF$_{1\alpha}$, amide,
3-oxa-3,7-inter-m-phenylene-4,5,6-trinor-(15R)-15-methyl-19,20-didehydro-PGF$_{1\alpha}$, amide,
3-oxa-3,7-inter-m-phenylene-4,5,6-trinor-13,14-dihydro-19,20-didehydro-PGF$_{1\alpha}$, amide,
11-deoxy-19,20-didehydro-PGF$_{2\alpha}$, amide,
11-deoxy-2,2-difluoro-19,20-didehydro-PGF$_{2\alpha}$, amide,
11-deoxy-4,5,19,20-tetradehydro-PGF$_{1\alpha}$, amide,
11-deoxy-4,5,19,20-tetradehydro-(15S)-15-methyl-PGF$_{1\alpha}$, amide,
11-deoxy-4,5,19,20-tetradehydro-(15R)-15-methyl-PGF$_{1\alpha}$, amide,
11-deoxy-2,3,19,20-tetradehydro-PGF$_{1\alpha}$, amide,
11-deoxy-2,3,19,20-tetradehydro-16,16-dimethyl-PGF$_{1\alpha}$, amide,
11-deoxy-2,3,19,20-tetradehydro-16,16-difluoro-PGF$_{1\alpha}$, amide,
11-deoxy-19,20-didehydro-PGF$_{1\alpha}$, amide,
11-deoxy-16,16-dimethyl-19,20-didehydro-PGF$_{1\alpha}$, amide,
11-deoxy-16,16-difluoro-19,20-didehydro-PGF$_{1\alpha}$, amide,
11-deoxy-2,2-difluoro-19,20-didehydro-PGF$_{1\alpha}$, amide,
11-deoxy-3-oxa-3,7-inter-m-phenylene-4,5,6-trinor-19,20-didehydro-PGF$_{1\alpha}$, amide,
11-deoxy-3-oxa-3,7-inter-m-phenylene-4,5,6-trinor-15(S)-15-methyl-19,20-didehydro-PGF$_{1\alpha}$, amide,
11-deoxy-3-oxa-3,7-inter-m-phenylene-4,5,6-trinor-15(R)-15-methyl-19,20-didehydro-PGF$_{1\alpha}$, amide,
11-deoxy-3-oxa-3,7-inter-m-phenylene-4,5,6-trinor-13,14-dihydro-19,20-didehydro-PGF$_{1\alpha}$, amide,
11-deoxy-11α-hydroxymethyl-19,20-didehydro-PGF$_{2\alpha}$, amide,
11-deoxy-11α-hydroxymethyl-2,2-difluoro-19,20-didehydro-PGF$_{2\alpha}$, amide,
11-deoxy-11α-hydroxymethyl-4,5,19,20-tetradehydro-PGF$_{1\alpha}$, amide,
11-deoxy-11α-hydroxymethyl-4,5,19,20-tetradehydro-15(S)-15-methyl-PGF$_{1\alpha}$, amide,
11-deoxy-11α-hydroxymethyl-4,5,19,20-tetradehydro-15(R)-15-methyl-PGF$_{1\alpha}$, amide,
11-deoxy-11α-hydroxymethyl-2,3,19,20-tetradehydro-PGF$_{1\alpha}$, amide,
11-deoxy-11α-hydroxymethyl-2,3,19,20-tetradehydro-16,16-dimethyl-PGF$_{1\alpha}$, amide,
11-deoxy-11α-hydroxymethyl-2,3,19,20-tetradehydro-16,16-difluoro-PGF$_{1\alpha}$, amide,
11-deoxy-11α-hydroxymethyl-19,20-didehydro-PGF$_{1\alpha}$, amide,
11-deoxy-11α-hydroxymethyl-16,16-dimethyl-19,20-didehydro-PGF$_{1\alpha}$, amide,
11-deoxy-11α-hydroxymethyl-16,16-difluoro-19,20-didehydro-PGF$_{1\alpha}$, amide,
11-deoxy-11α-hydroxymethyl-2,2-difluoro-19,20-didehydro-PGF$_{1\alpha}$, amide,
11-deoxy-11α-hydroxymethyl-3-oxa-3,7-inter-m-phenylene-4,5,6-trinor-19,20-didehydro-PGF$_{1\alpha}$, amide,
11-deoxy-11α-hydroxymethyl-3-oxa-3,7-inter-m-phenylene-4,5,6-trinor-(15S)-15-methyl-19,20-didehydro-PGF$_{1\alpha}$, amide,
11-deoxy-11α-hydroxymethyl-3-oxa-3,7-inter-m-phenylene-4,5,6-trinor-(15R)-15-methyl-19,20-didehydro-PGF$_{1\alpha}$, amide,
11-deoxy-11α-hydroxymethyl-3-oxa-3,7-interm-m-phenylene-4,5,6-trinor-13,14-dihydro-19,20-didehydro-PGF$_{1\alpha}$, amide.

Likewise following the procedures disclosed herein, there are prepared the corresponding 19,20-didehydro-PGF$_{1\beta}$, —PGE$_1$, and 9-deoxo-9-methylene-PGE amides within the scope of formula III wherein R$_1$ is —C(O)—NH$_2$.

E. Wherein R$_1$ is —C(O)NH—SO$_2$—CH$_3$.
19,20-didehydro-PGF$_{2\alpha}$, methanesulfonylamide,
16,16-dimethyl-19,20-didehydro-PGF$_{2\alpha}$, methanesulfonylamide,
2,3,19,20-tetradehydro-PGF$_{1\alpha}$, methanesulfonylamide,
2,3,19,20-tetradehydro-16,16-dimethyl-PGF$_{1\alpha}$, methanesulfonylamide,
2,3,19,20-tetradehydro-16,16-difluoro-PGF$_{1\alpha}$, methanesulfonylamide,
19,20-didehydro-PGF$_{1\alpha}$, methanesulfonylamide,
16,16-difluoro-19,20-didehydro-PGF$_{1\alpha}$, methanesulfonylamide,
11-deoxy-19,20-didehydro-PGF$_{2\alpha}$, methanesulfonylamide,
11-deoxy-16,16-dimethyl-19,20-didehydro-PGF$_{2\alpha}$, methanesulfonylamide,
11-deoxy-2,3,19,20-tetradehydro-PGF$_{1\alpha}$, methanesulfonylamide,
11-deoxy-2,3,19,20-tetradehydro-16,16-dimethyl-PGF$_{1\alpha}$, methanesulfonylamide,
11-deoxy-2,3,19,20-tetradehydro-16,16-difluoro-PGF$_{1\alpha}$, methanesulfonylamide,
11-deoxy-19,20-didehydro-PGF$_{1\alpha}$, methanesulfonylamide
11-deoxy-16,16-difluoro-19,20-didehydro-PGF$_{1\alpha}$, methanesulfonylamide,
11-deoxy-11α-hydroxymethyl-19,20-didehydro-PGF$_{2\alpha}$, methanesulfonylamide,
11-deoxy-11α-hydroxymethyl-16,16-dimethyl-19,20-didehydro-PGF$_{2\alpha}$, methanesulfonylamide,
11-deoxy-11α-hydroxymethyl-2,3,19,20-tetradehydro-PGF$_{1\alpha}$, methanesulfonylamide,
11-deoxy-11α-hydroxymethyl-2,3,19,20-tetradehydro-16,16-dimethyl-PGF$_{1\alpha}$, methanesulfonylamide,
11-deoxy-11α-hydroxymethyl-2,3,19,20-tetradehydro-16,16-difluoro-PGF$_{1\alpha}$, methanesulfonylamide,
11-deoxy-11α-hydroxymethyl-19,20-didehydro-PGF$_{1\alpha}$, methanesulfonylamide,
11-deoxy-11α-hydroxymethyl-16,16-difluoro-19,20-didehydro-PGF$_{1\alpha}$, methanesulfonylamide.

Likewise following the procedures disclosed herein, there are prepared the corresponding 19,20-didehydro-PGF$_{1\beta}$, -PGE$_1$, and 9-deoxo-9-methylene-PGE methanesulfonylamides within the scope of formula III wherein R$_1$ is —C(O)—NH—SO$_2$—CH$_3$.

II. 19-Hydroxy Prostaglandin-Type Compounds of Formula IV

For every 19,20-didehydro compound listed above, including tetradehydro or hexadehydro compounds having the 19,20-didehydro feature, there is a corresponding 19-hydroxy prostaglandin-type compound, (19R) or (19S), and the mixed (19R,S) or "19(±)" hydroxy compounds.

Following the procedures disclosed herein, all of the corresponding 19-hydroxy-PGF$_\alpha$, -PGF$_\beta$, -PGE, and -9-deoxo-9-methylene-PGE compounds within the scope of formula IV are prepared as follows:

A. Wherein R$_{19}$ is —COOR$_6$, specifically the methyl esters, free acids, and sodium salts; for example corresponding to 16,16-dimethyl-19,20-didehydro-PGE$_{2\alpha}$, methyl ester listed above there are:
16,16-dimethyl-(19R)-19-hydroxy-PGF$_{2\alpha}$, methyl ester,
16,16-dimethyl-(19S)-19-hydroxy-PGF$_{2\alpha}$, methyl ester,
16,16-dimethyl-(19R,S)-19-hydroxy-PGF$_{2\alpha}$, methyl ester.

B. Wherein R$_{19}$ is —CH$_2$OH.
C. Wherein R$_{19}$ is —CH$_2$NH$_2$.
D. Wherein R$_{19}$ is —C(O)—NH$_2$.
E. Wherein R$_{19}$ is —C(O)—NH—SO$_2$—CH$_3$.

III. 19-Keto Prostaglandin-Type Compounds of Formula V

For every 19,20-didehydro compound listed above, including tetradehydro or hexadehydro compounds having the 19,20-didehydro feature, there is a corresponding 19-keto prostaglandin-type compound.

Following the procedures disclosed herein, all of the corresponding 19-keto-PGF$_\alpha$-PGF$_\beta$, -PGE, and 9-deoxo-9-methylene-PGE compounds within the scope of formula V are prepared as follows:

A. Wherein R$_{20}$ is —COOR$_6$, specifically the methyl esters, free acids, and sodium salts; for example corresponding to 16,16-difluoro-19,20-didehydro-PGF$_{2\alpha}$, methyl ester listed above there is: 16,16-difluoro-19-keto-PGF$_{2\alpha}$, methyl ester.

B. Wherein R$_{20}$ is —CH$_2$OH.
C. Wherein R$_{20}$ is —CH$_2$NH$_2$.
D. Wherein R$_{20}$ is —C(O)—NH$_2$.
E. Wherein R$_{20}$ is —C(O)—NH—SO$_2$—CH$_3$.

IV. 19-Hydroxy-19-Methyl Prostaglandin-Type Compounds of Formula VI

For every 19,20-didehydro compound listed above, including tetradehydro or hexadehydro compounds having the 19,20-didehydro feature, there is a corresponding 19-hydroxy-19-methyl prostaglandin-type compound.

Following the procedures disclosed herein, all of the corresponding 19-hydroxy-19-methyl-PGF$_\alpha$, -PGF$_\beta$, -PGE, and 9-deoxo-9-methylene-PGE compounds within the scope of formula VI are prepared, as follows:

A. Wherein R$_1$ is —COOR$_6$, specifically the methyl esters, free acids, and sodium salts; for example corresponding to 19,20-didehydro-PGF$_{2\alpha}$, methyl ester listed above there is 19-hydroxy-19-methyl-PGF$_{2\alpha}$, methyl ester.

B. Wherein R$_1$; is —CH$_2$OH.
C. Wherein R$_1$ is —CH$_2$NH$_2$.
D. Wherein R$_1$ is —C(O)—NH$_2$.
E. Wherein R$_1$ is —C(O)—NH—SO$_2$—CH$_3$.

FORMULAS

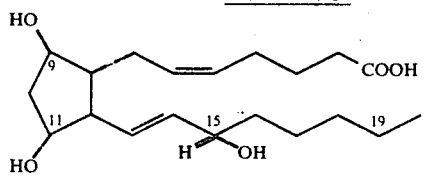

I

-continued
FORMULAS

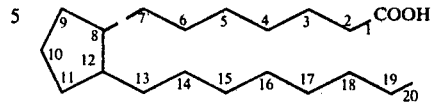

II

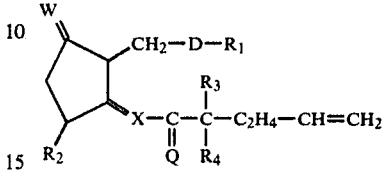

III

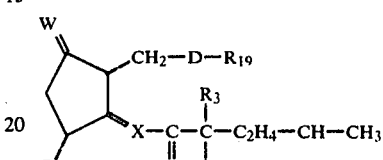

IV

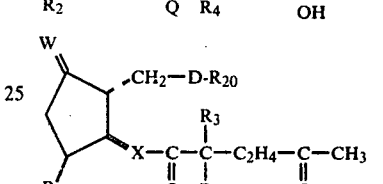

V

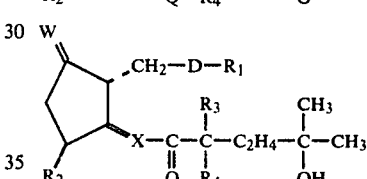

VI

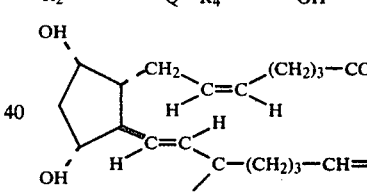

VII

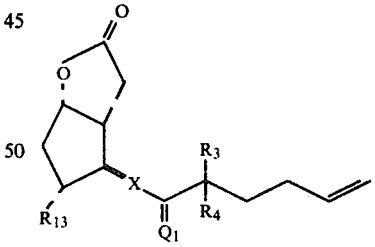

VIII

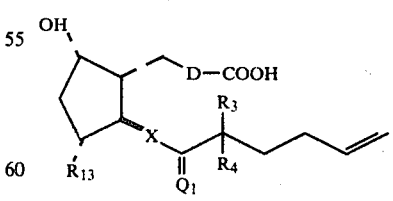

IX

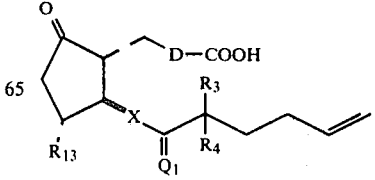

XI

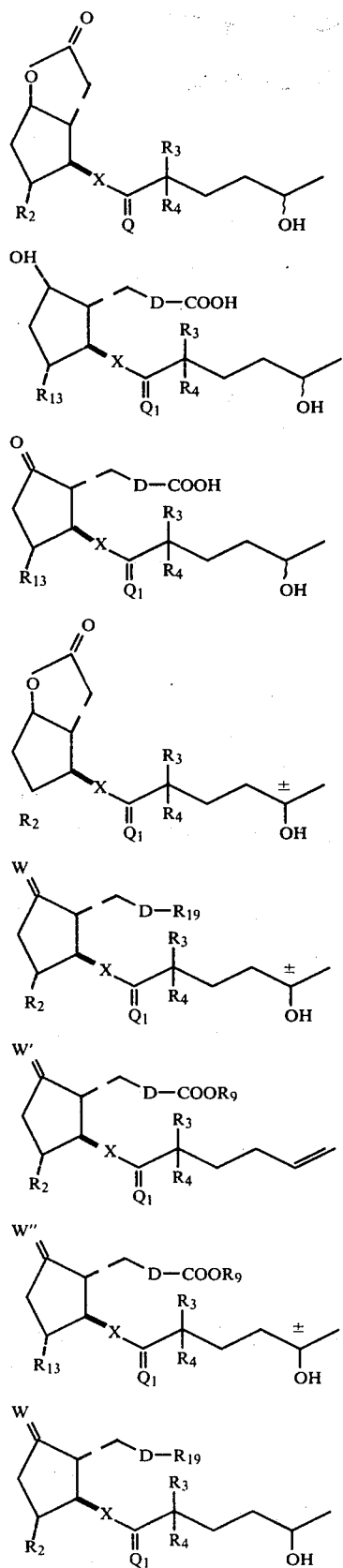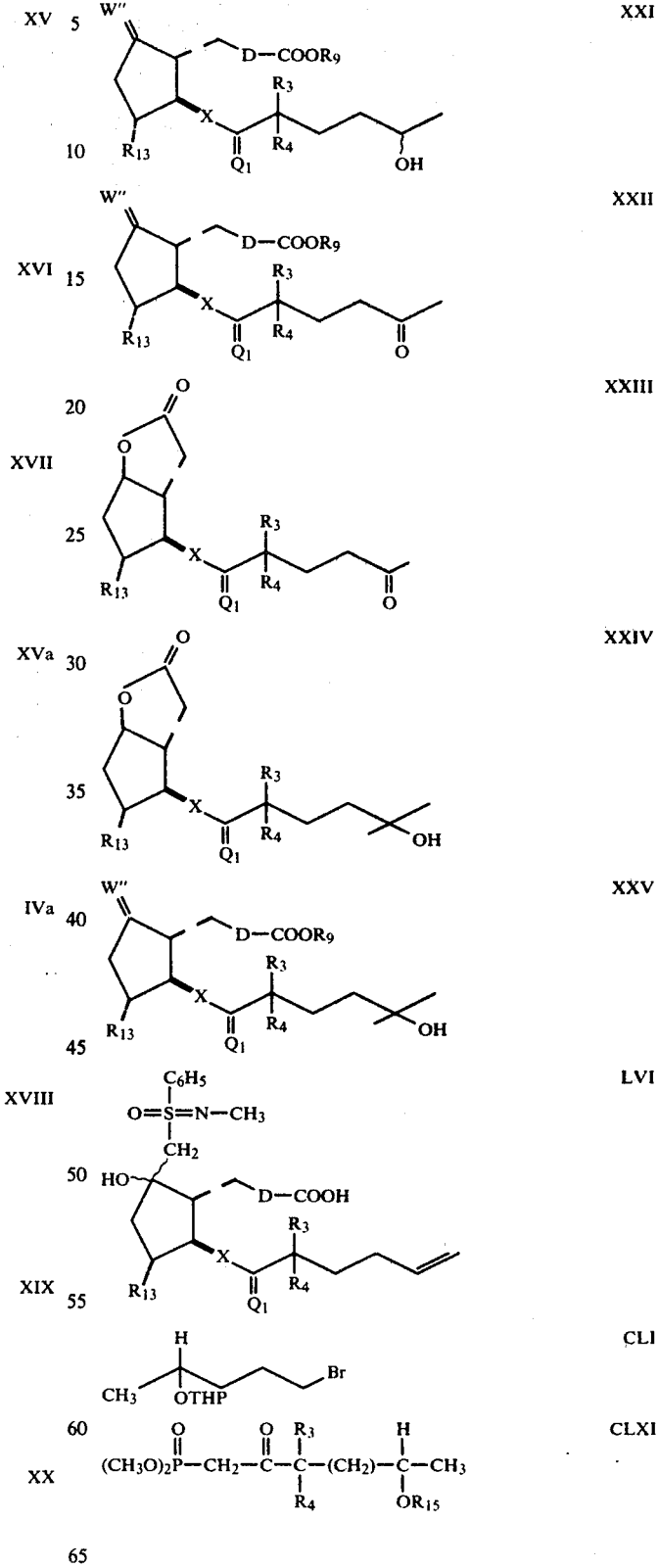

CHART 1
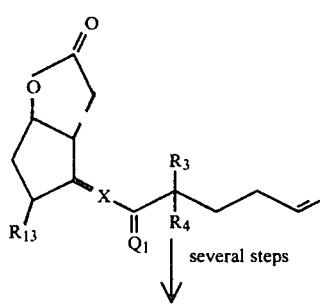
VIII
several steps
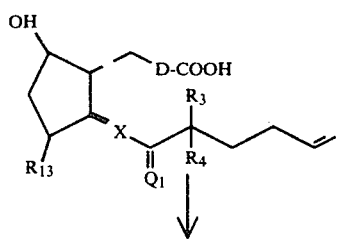
IX
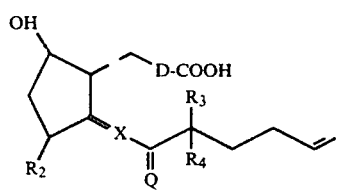
X
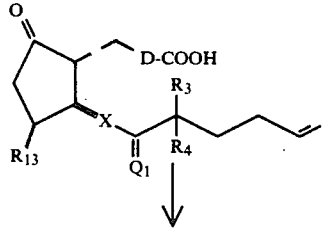
XI
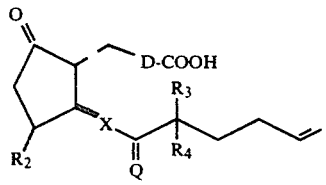
XII
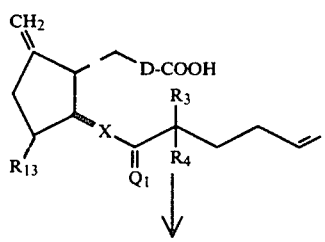
XIII
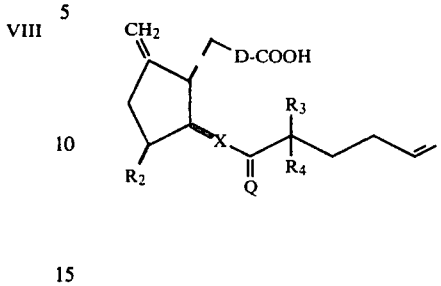
XIV
CHART 2
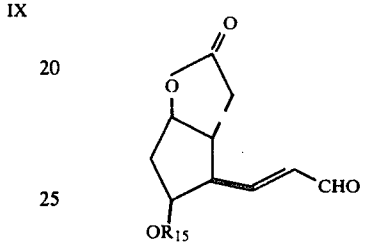
XXVI
step (a)
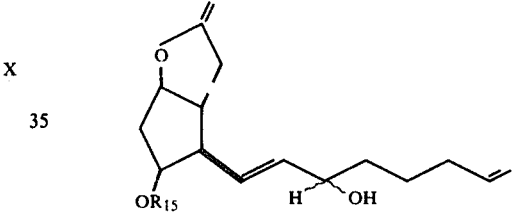
XXVII
several steps
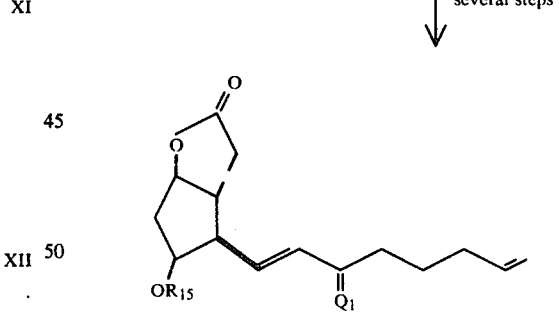
XXVIII
CHART 3
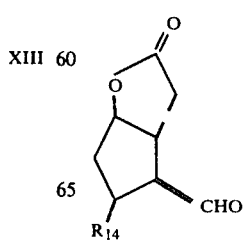
XXXVII
step (a)

-continued
CHART 3
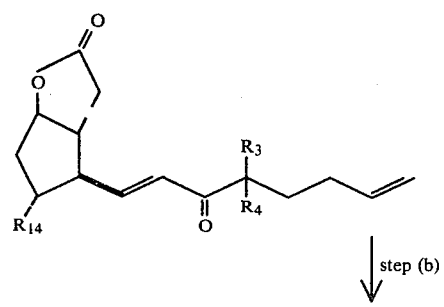
XXXVIII
↓ step (b)
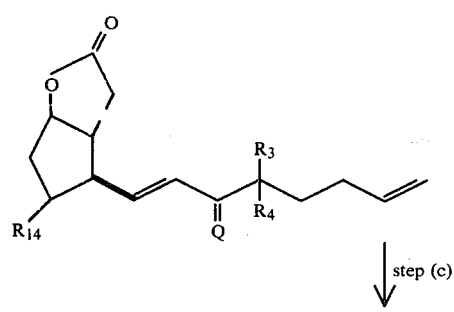
XXXIX
↓ step (c)
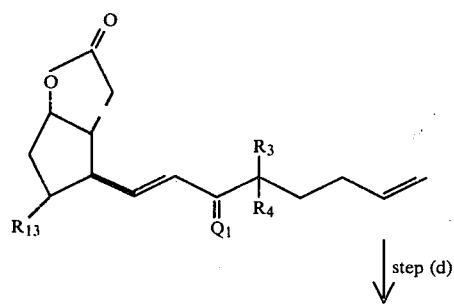
XL
↓ step (d)
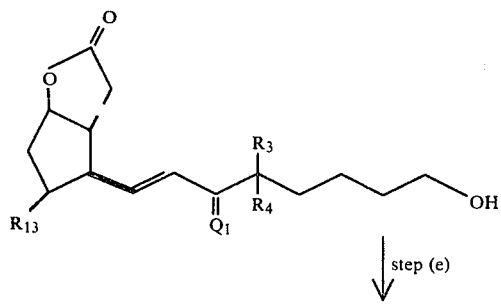
XLI
↓ step (e)
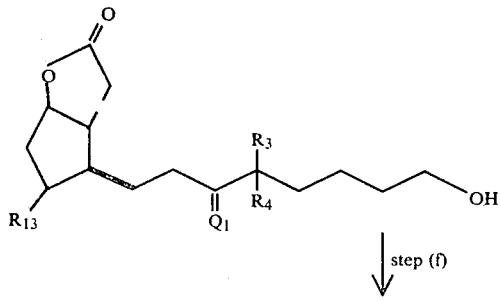
XLII
↓ step (f)
-continued
CHART 3
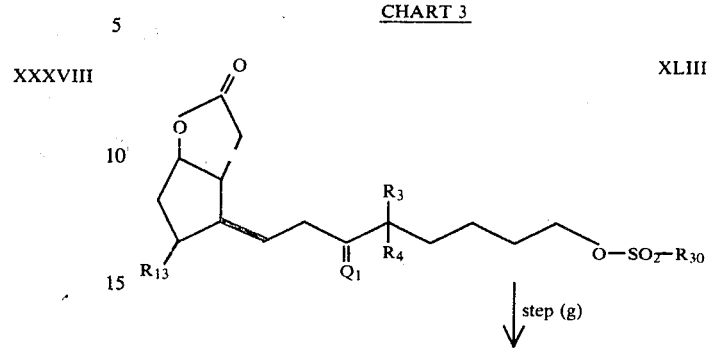
XLIII
↓ step (g)
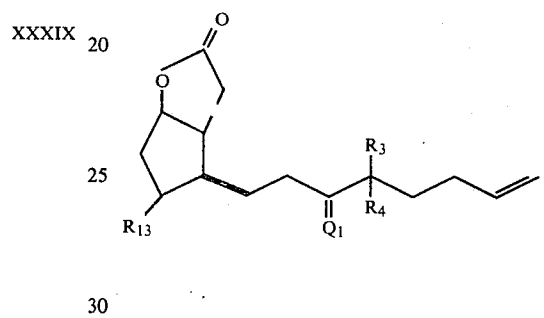
XLIV
CHART 4
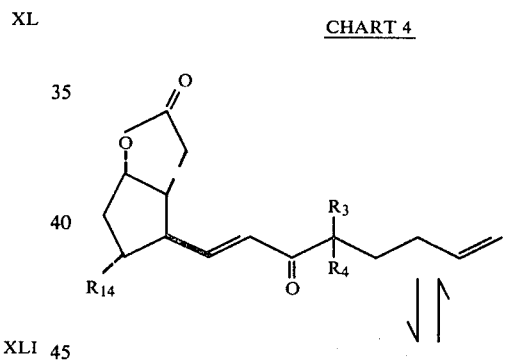
XXXVIII
⇅
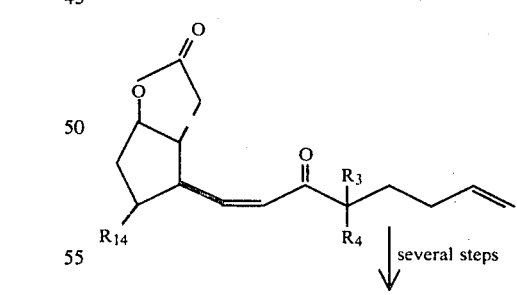
XLV
↓ several steps
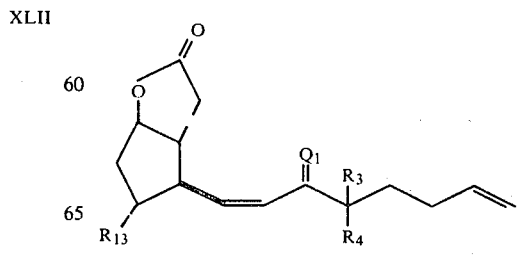
XLVI

CHART 5
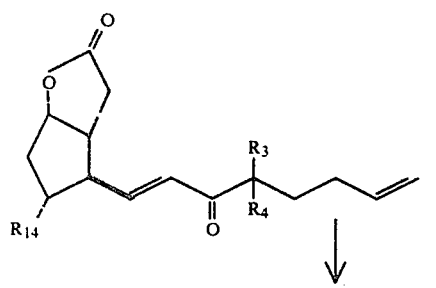 XXXVIII
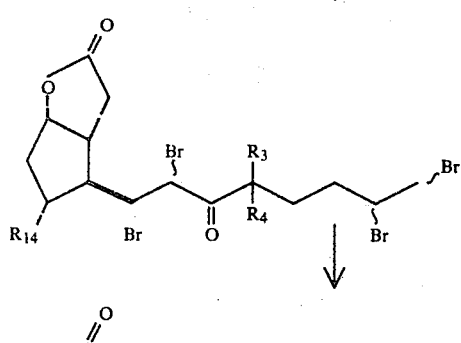 XLVII
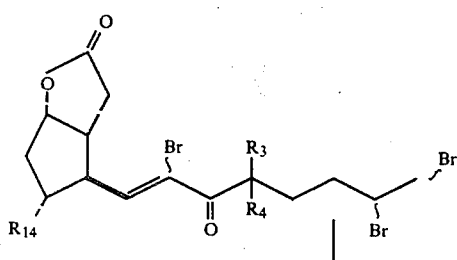 XLVIII
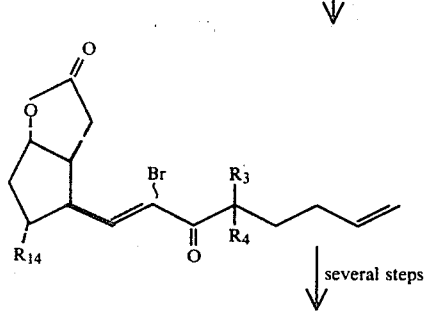 XLIX
several steps
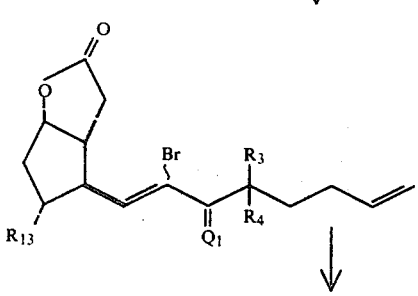 L
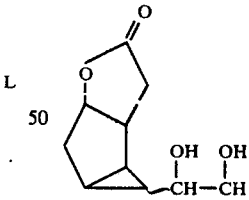 LI
-continued
CHART 5
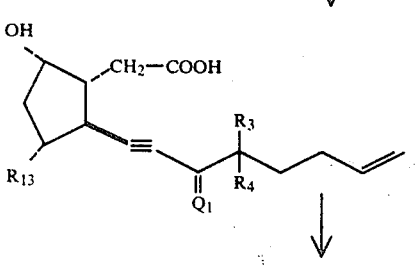 LII
CHART 6
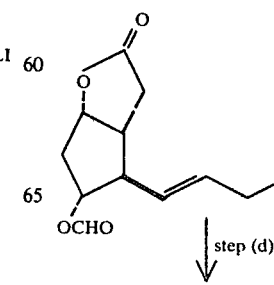 XXIX
step (a)
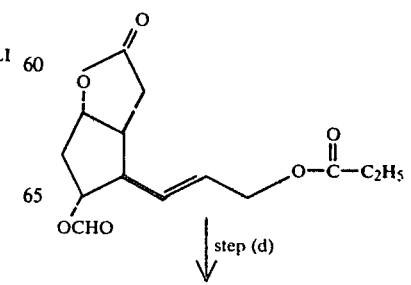 XXX
step (b)
XXXI
step (c)
XXXII
step (d)

CHART 6
-continued
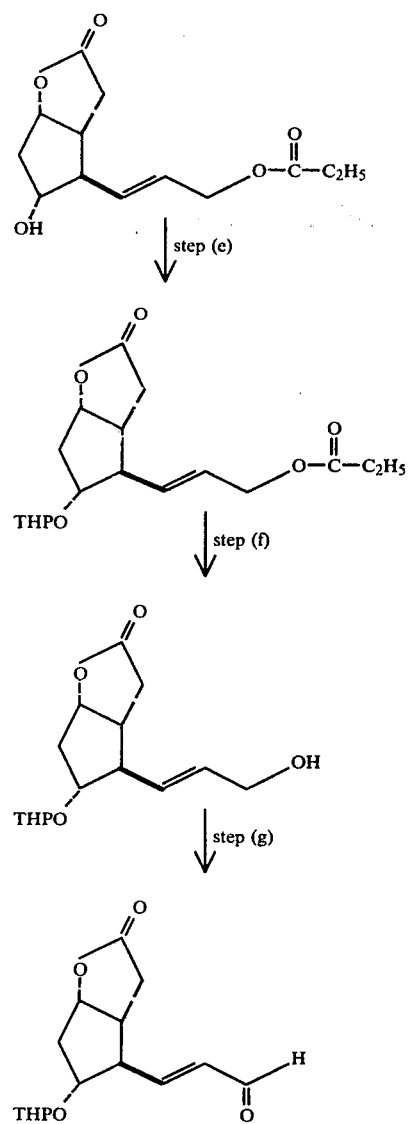
CHART 7
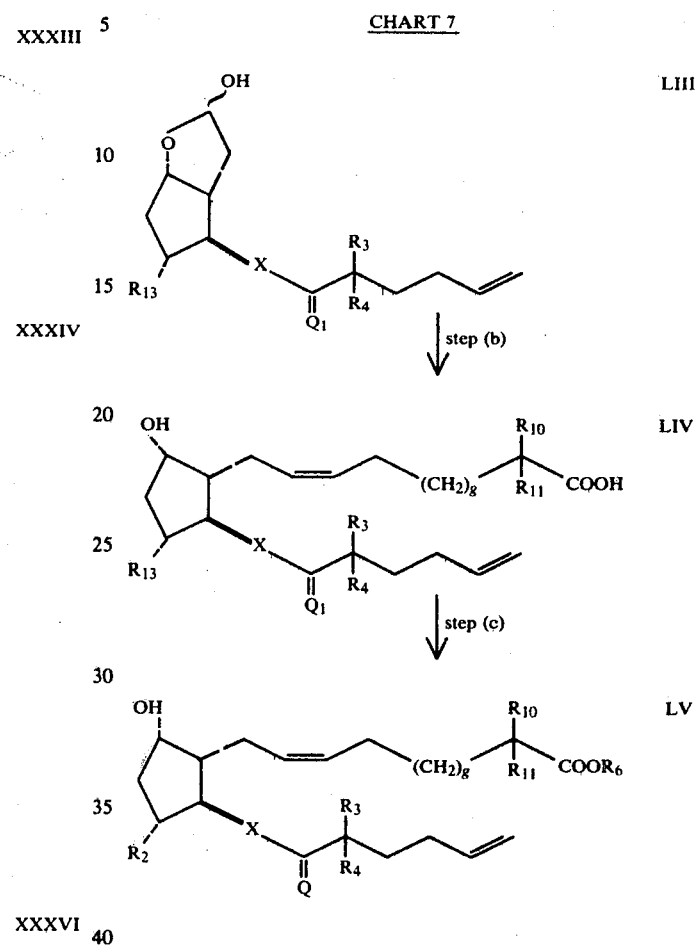
CHART 7
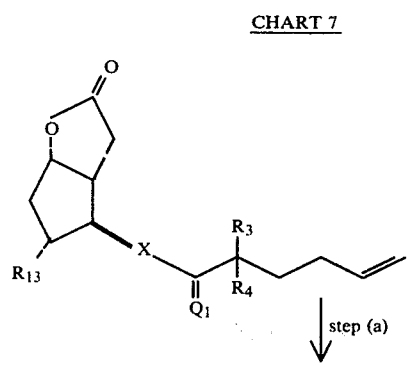
CHART 8
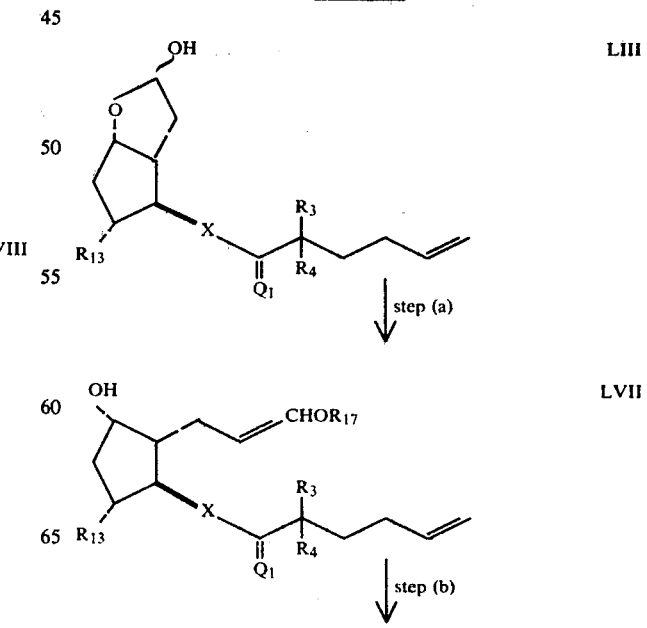

CHART 8
-continued
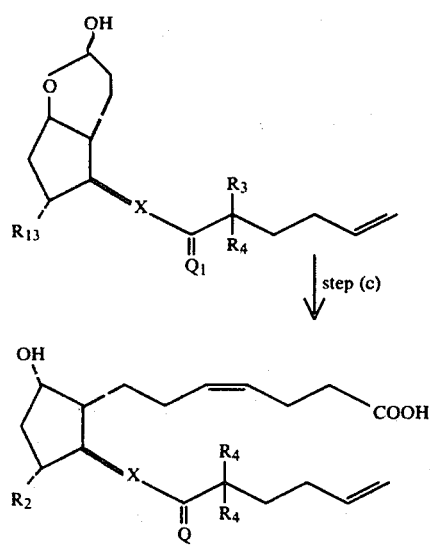
CHART 9
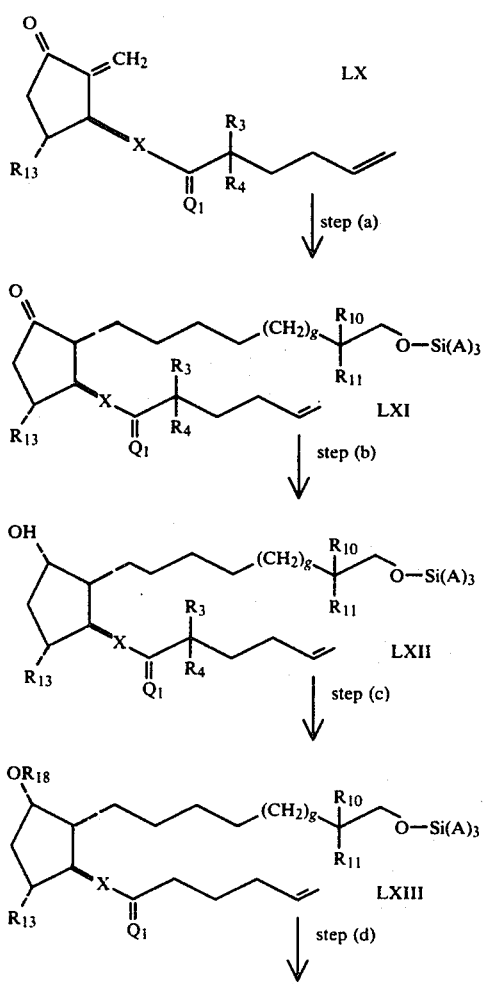
-continued
CHART 9
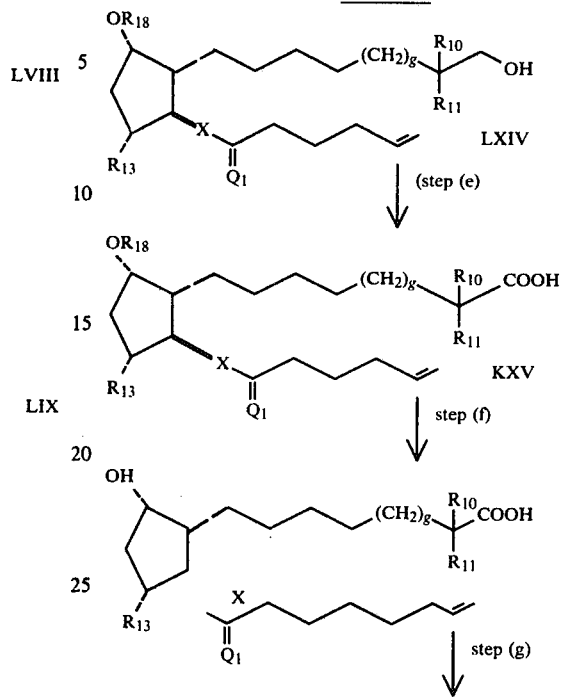
CHART 10
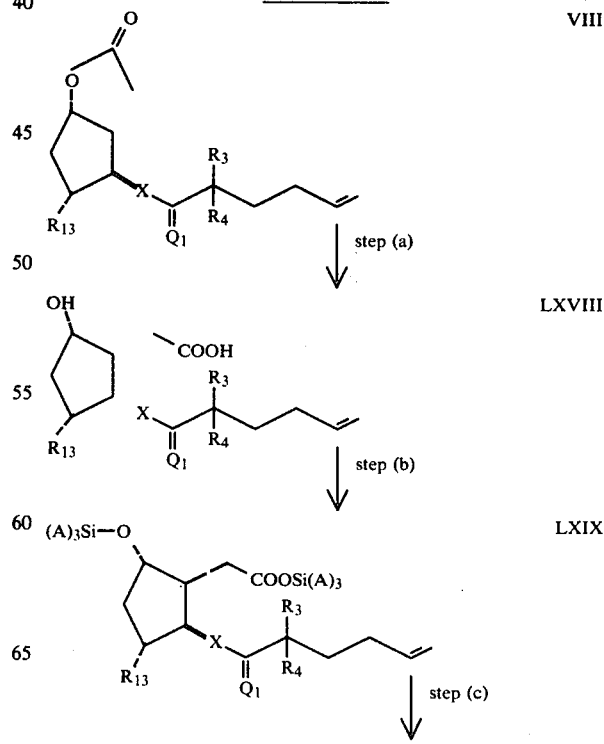

-continued
CHART 10
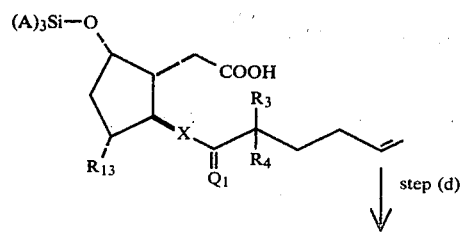
LXX
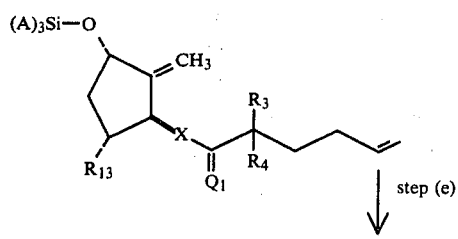
LXXI
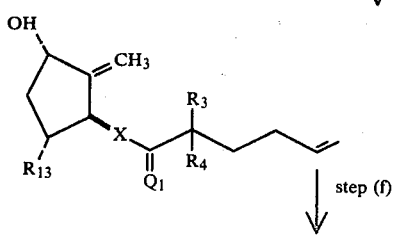
LXXII
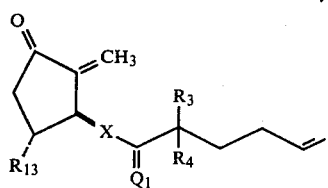
step (d)
step (e)
step (f)
CHART 11
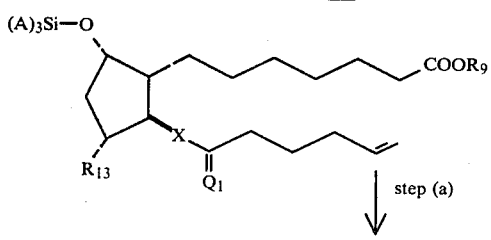
LXXIII
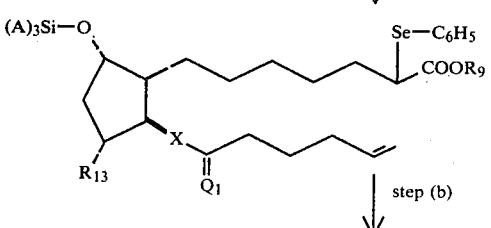
LXXIV
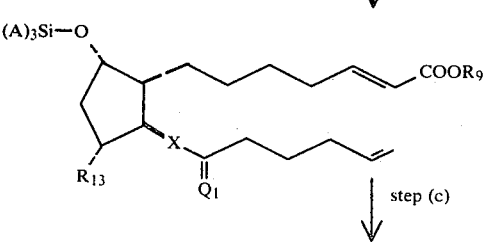
LXXV
step (a)
step (b)
step (c)
-continued
CHART 11
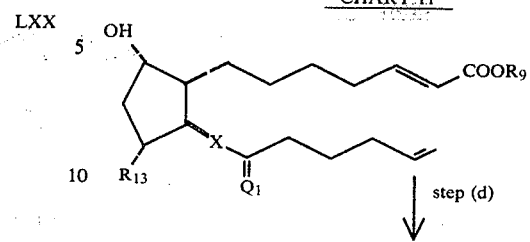
LXXVI
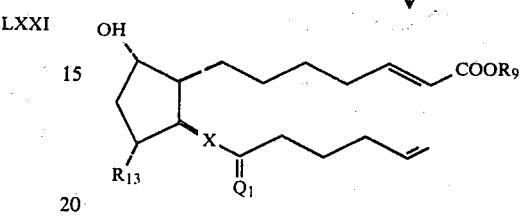
LXXVII
step (d)
CHART 12
LX
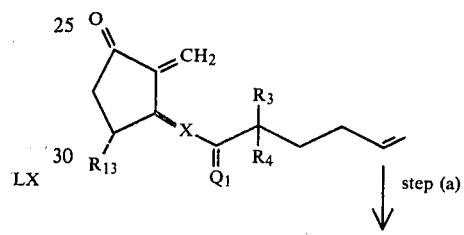
LXXVIII
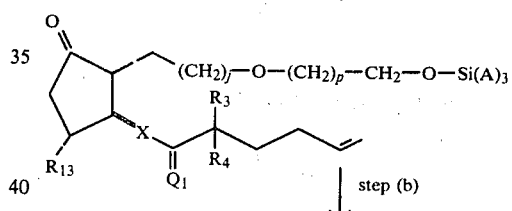
LXXIX
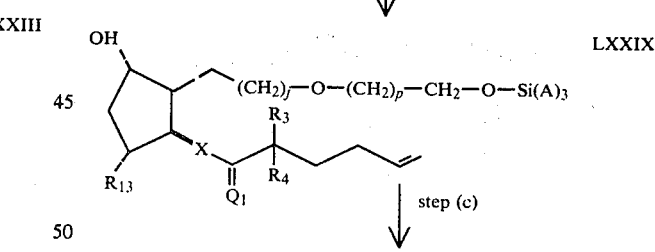
LXXX
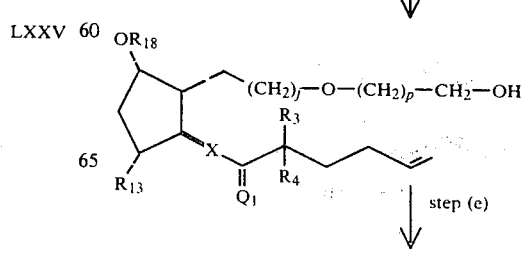
LXXXI
step (a)
step (b)
step (c)
step (d)
step (e)

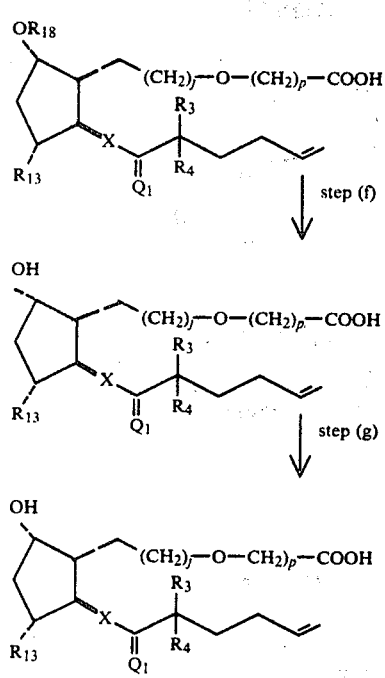

-continued
CHART 14
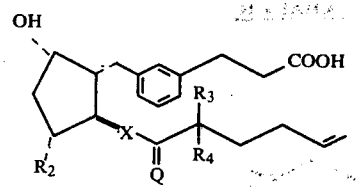
CHART 15
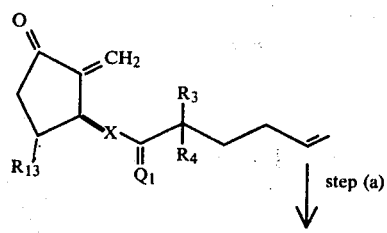
step (a)
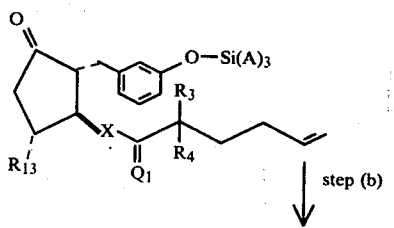
step (b)
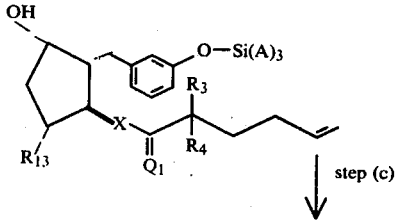
step (c)
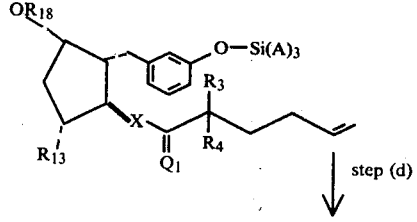
step (d)
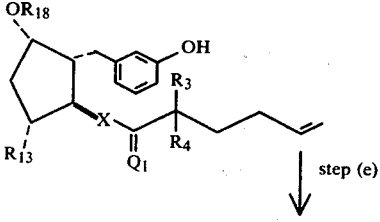
step (e)
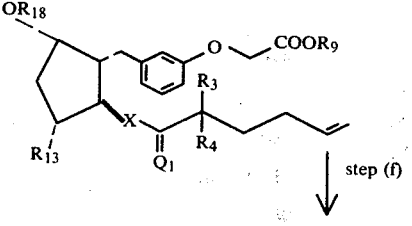
step (f)
-continued
CHART 15
XCIV 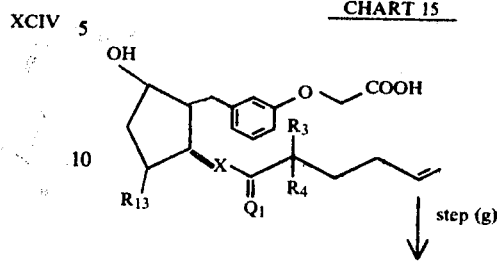
step (g)
LX 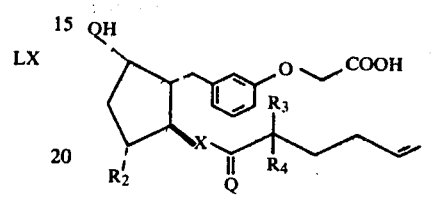 CI
XCV
CHART 16
CII 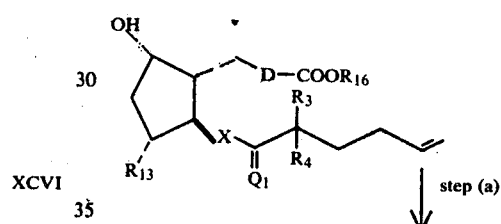
step (a)
XCVI
CIII 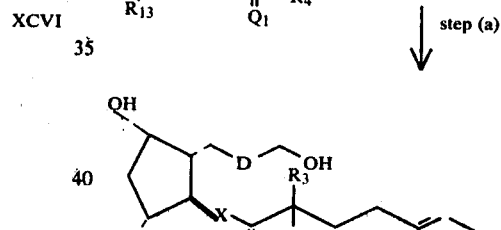
step (b)
XCVII
CIV 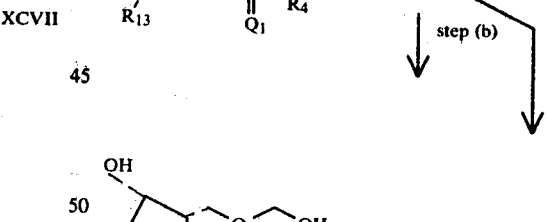
XCVIII
CV step (c)
XCIX 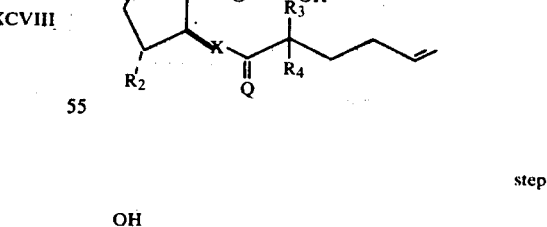
step (d)

-continued
CHART 16
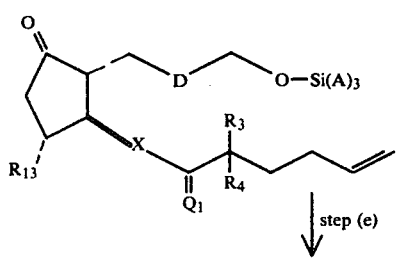
↓ step (e)
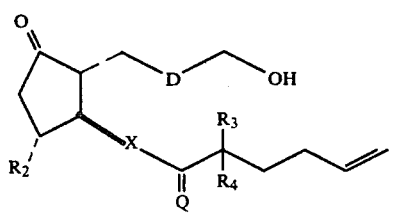
CHART 17
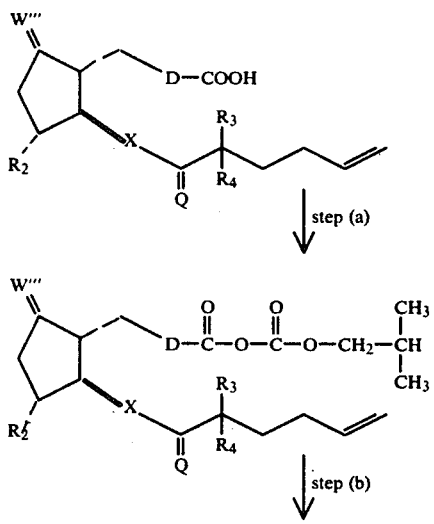
↓ step (d)
-continued
CHART 17
CXII
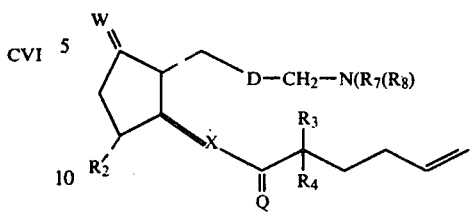
CHART 18
CXIII
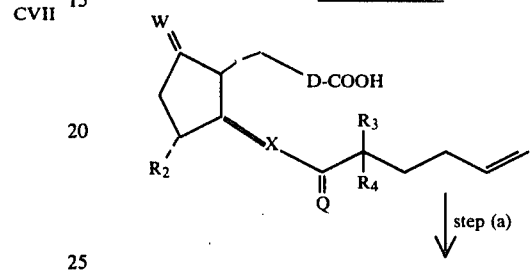
↓ step (a)
CXIV
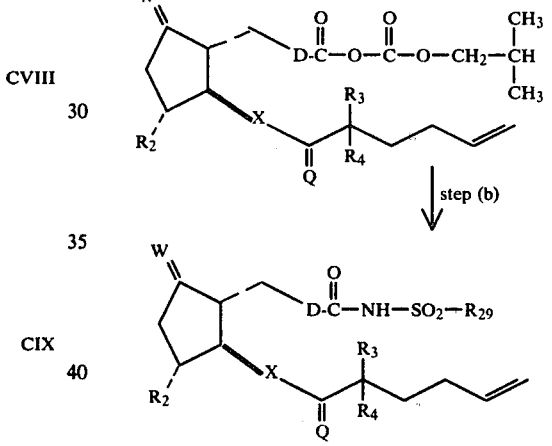
↓ step (b)
CXV
CHART 19
LIII
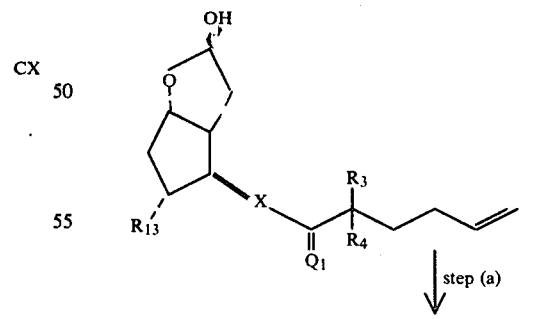
↓ step (a)
CXVI
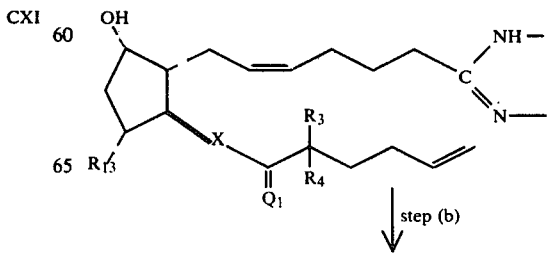
↓ step (b)

-continued
CHART 19
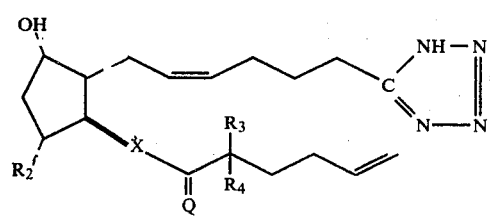
CXVII
CHART 20
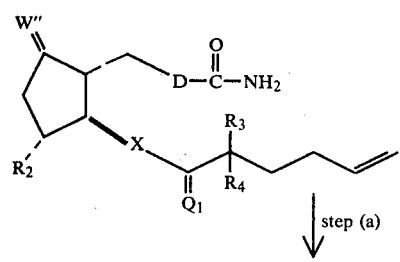
CXVIII
↓ step (a)
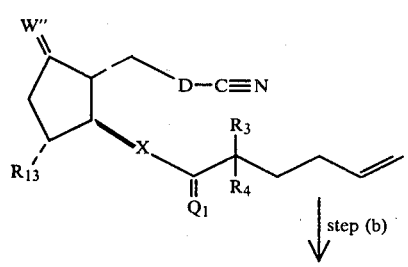
CXIX
↓ step (b)
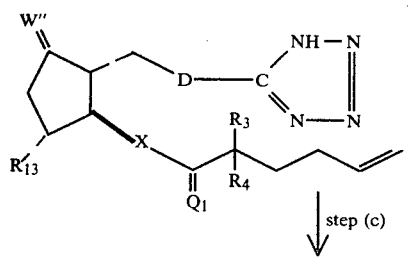
CXX
↓ step (c)
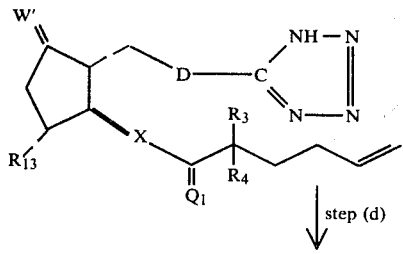
CXXI
↓ step (d)
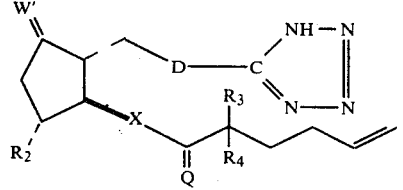
CXXII
CHART 21
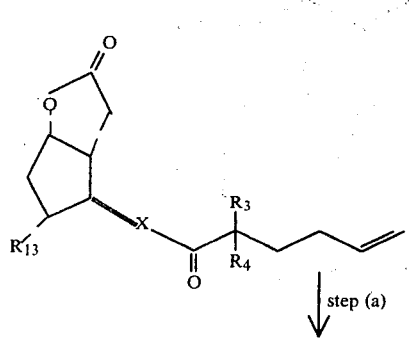
CXXIII
↓ step (a)
CXXIV
↓ step (b)
CXXV
↓ step (c)
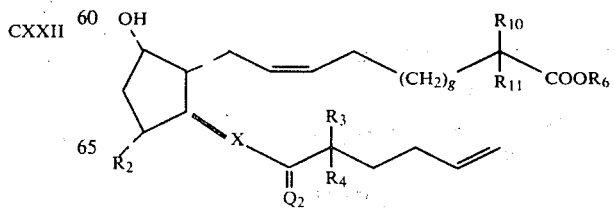
CXXVI
↓ step (d)
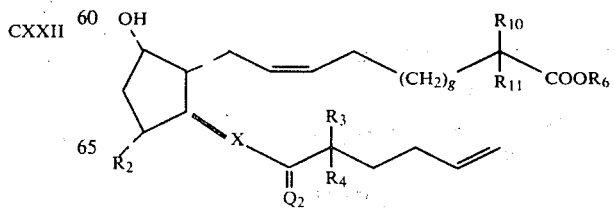
LV CHART 22
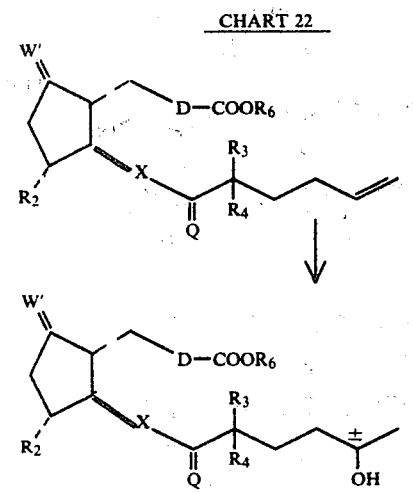
CHART 23
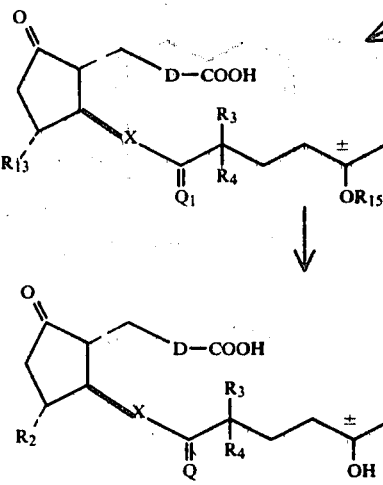
-continued
CHART 23
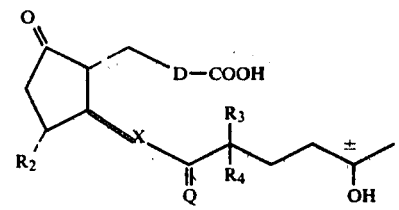
CHART 24
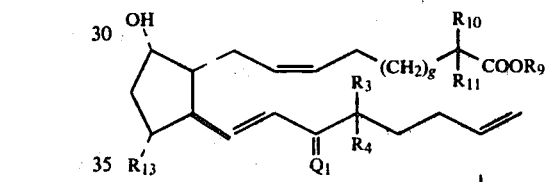

-continued
CHART 24
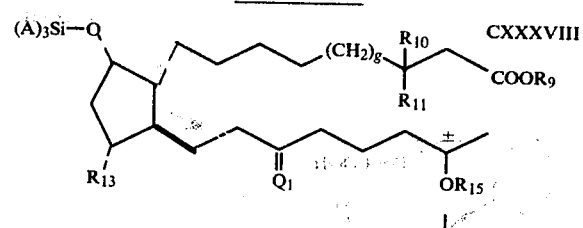
CXXXVIII
↓ step (e)
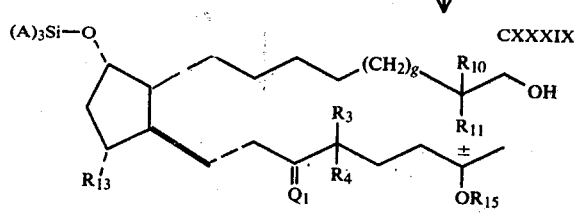
CXXXIX
↓ step (f)
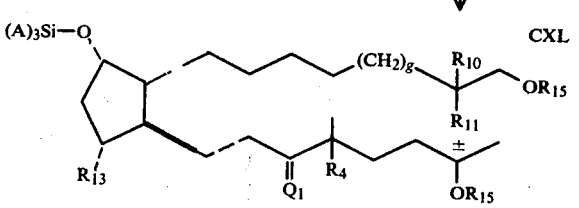
CXL
↓ step (g)
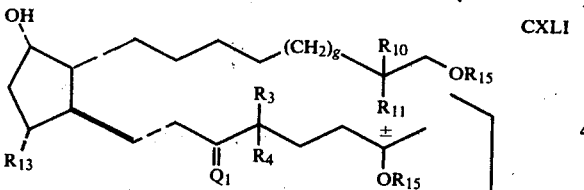
CXLI
↓ step (h)
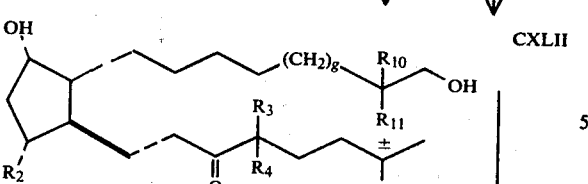
CXLII
↓ step (i)
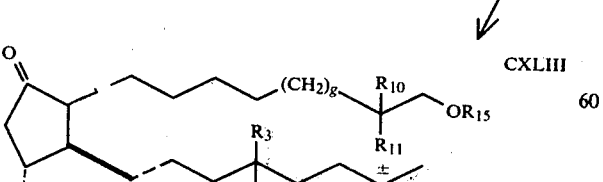
CXLIII
↓ step (j)
-continued
CHART 24
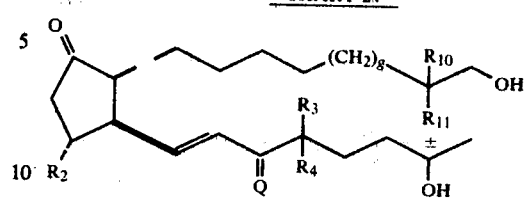
CXLIV
+
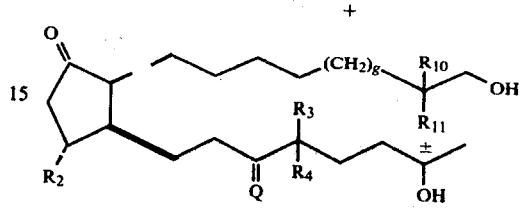
CXLV
CHART 25
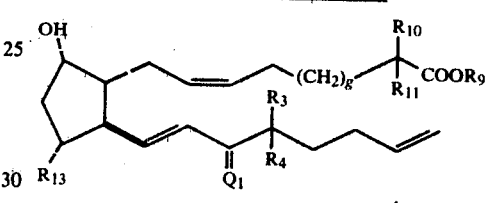
CXLVI
↓ step (a)
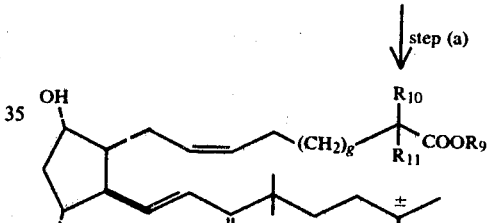
CXLVII
↓ step (b)
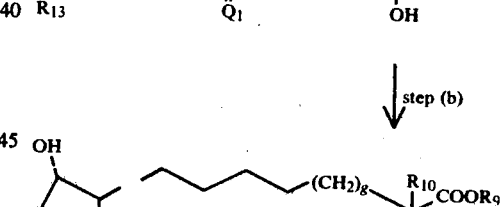
CXLVIII
↓ step (c)
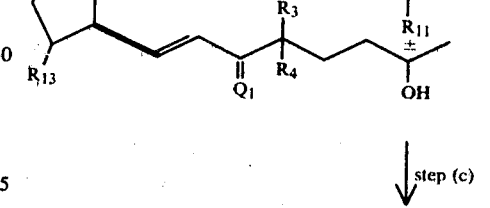
CXLIX
↓ step (d)

37
-continued
CHART 25
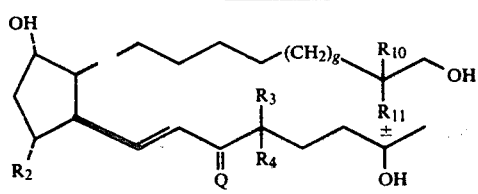
CHART 26
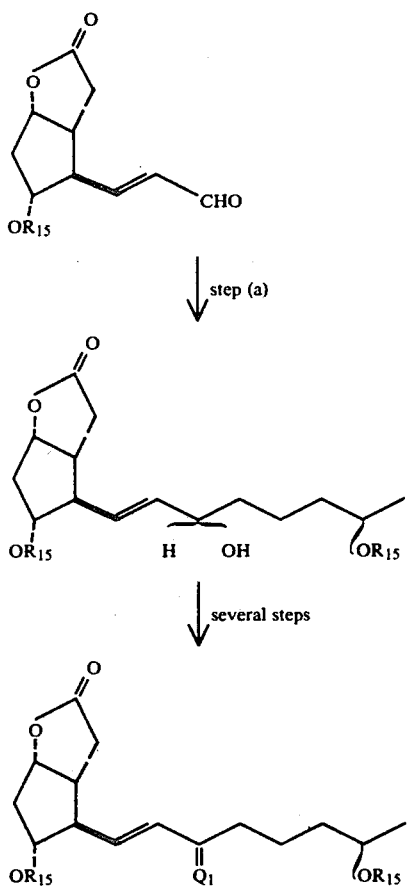
CHART 27
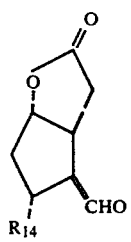
38
-continued
CHART 27
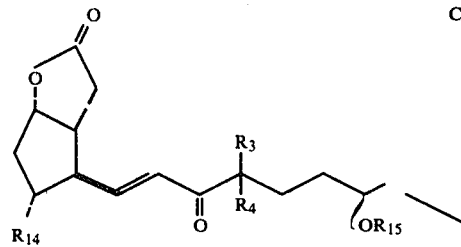
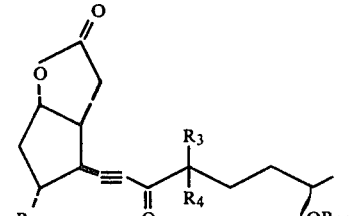
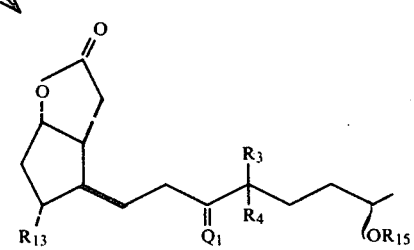

CHART 28
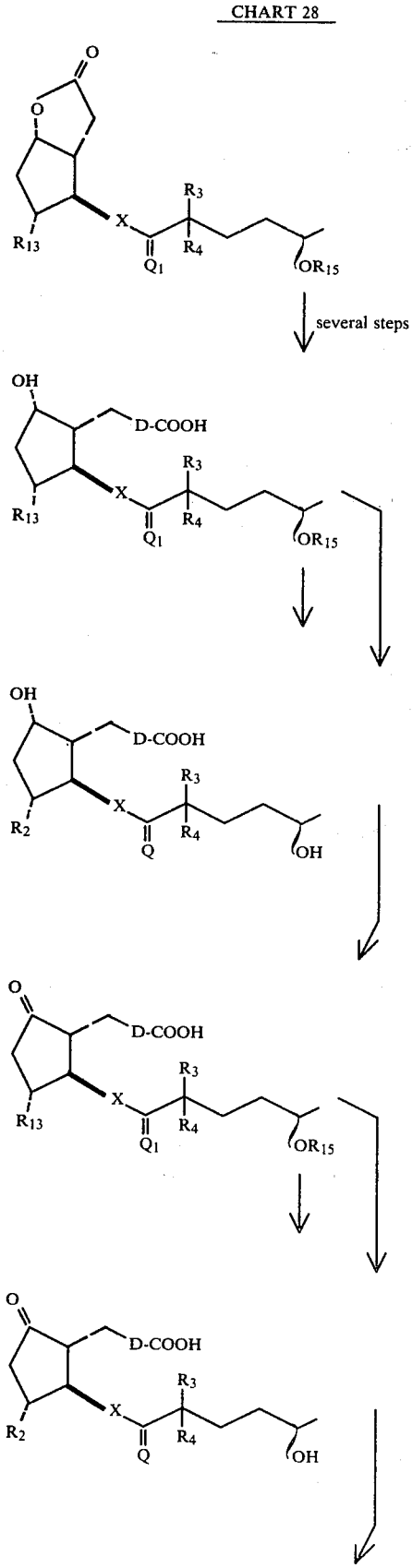
CHART 28 -continued
CHART 29
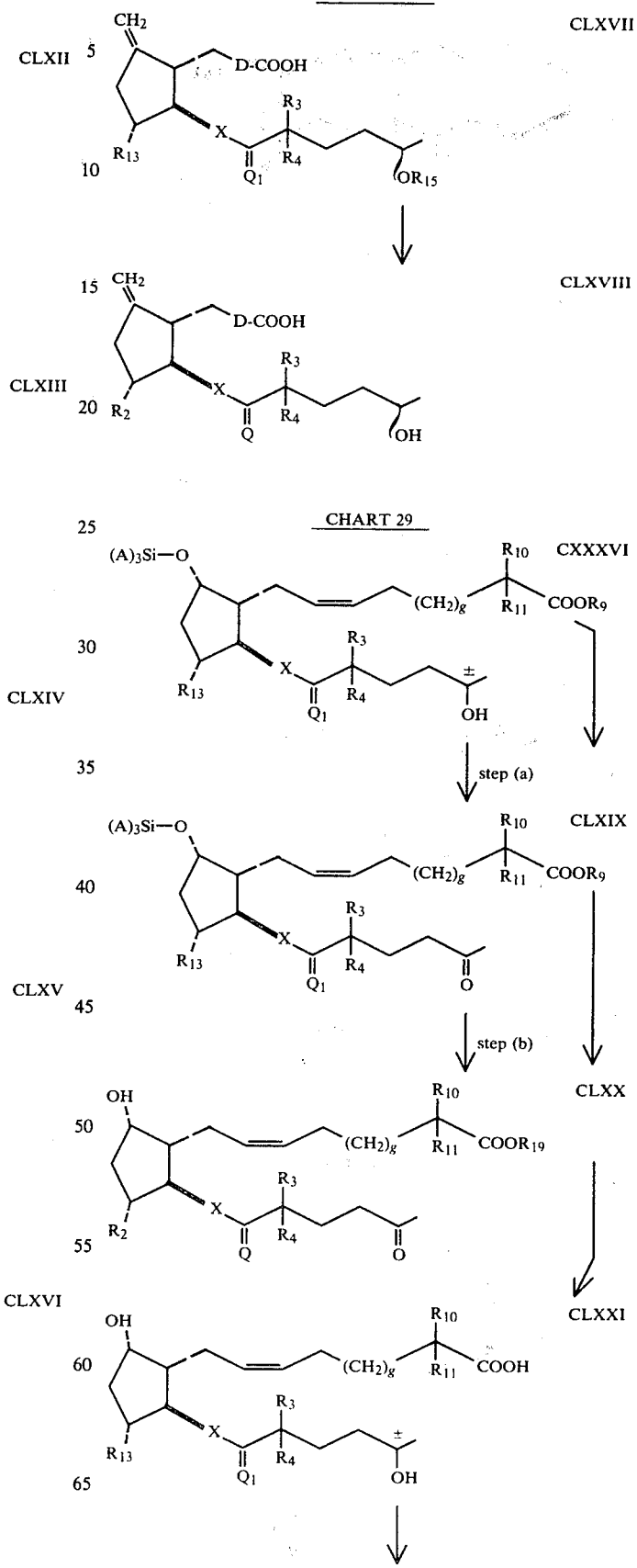

-continued
CHART 29
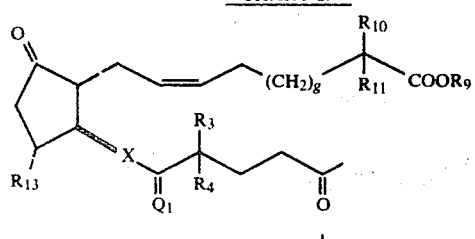
CLXXII
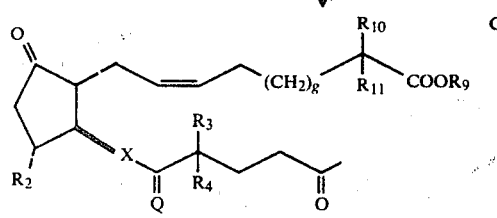
CLXXIII
CHART 30
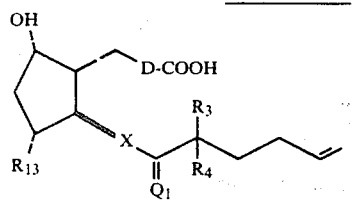
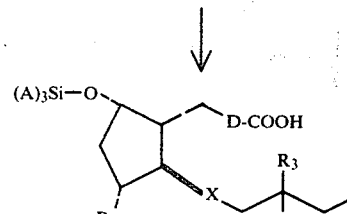
CLXXIV
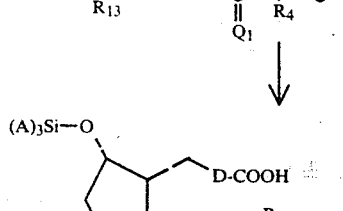
CLXXV
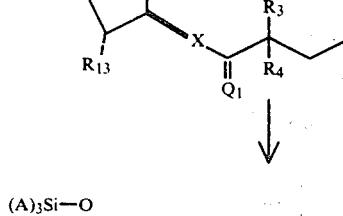
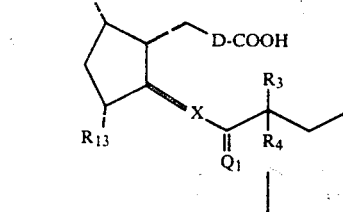
CLXXVI
-continued
CHART 30
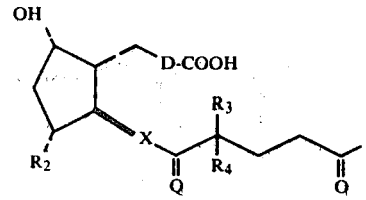
CLXXVII
CLXXVIII
IX
CLXXIX
CLXXX
CHART 31
CXLIX
CLXXXI
step (a)
step (b)

4,243,611
43
-continued
CHART 31
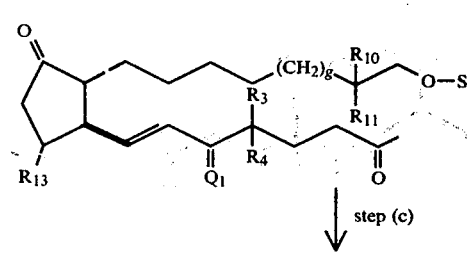
CLXXXII
↓ step (c)
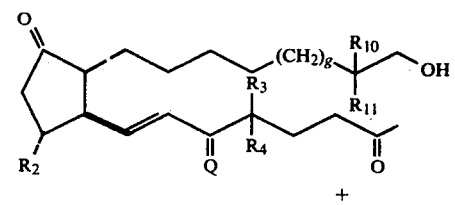
CLXXXIII
+
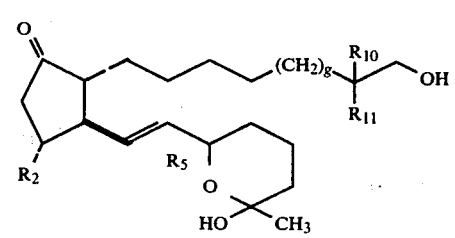
CLXXXIV
CHART 32
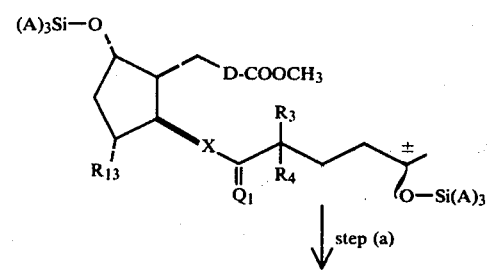
CLXXXV
↓ step (a)
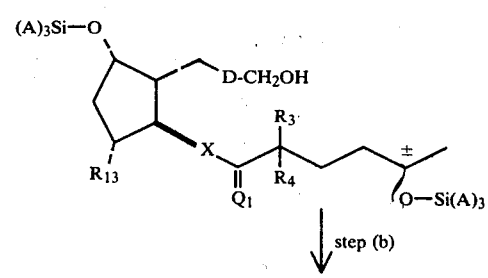
CLXXXVI
↓ step (b)
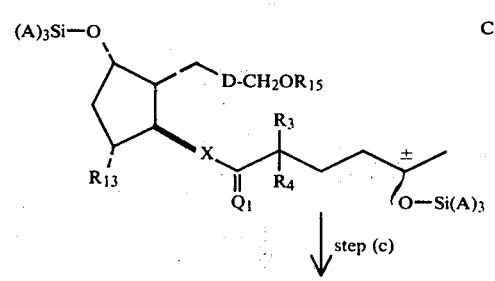
CLXXXVII
↓ step (c)
44
-continued
CHART 32
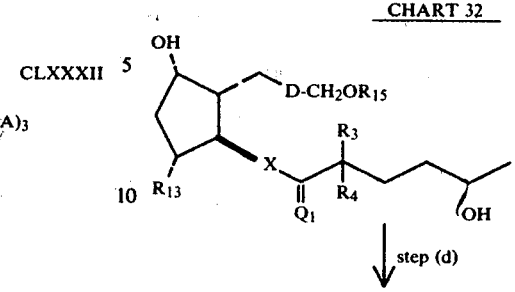
CLXXXVIII
↓ step (d)
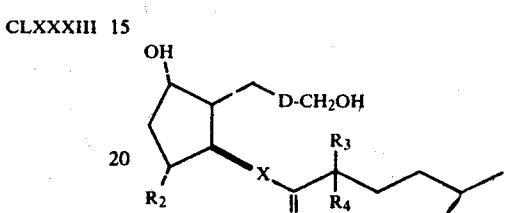
CLXXXIX
↓ step (e)
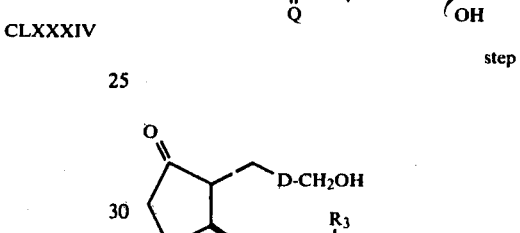
CXC
↓ step (f)
CXCI
CHART 33
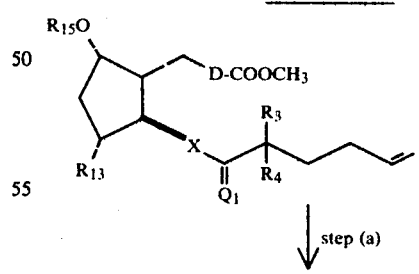
CXCII
↓ step (a)
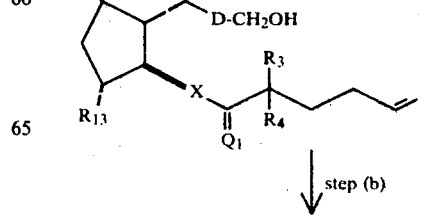
CXCIII
↓ step (b)

4,243,611
45
-continued
CHART 33
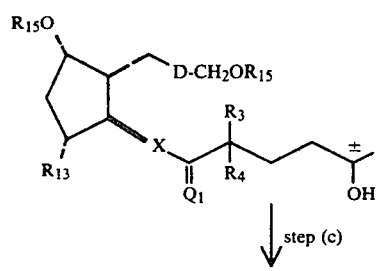
↓ step (c)
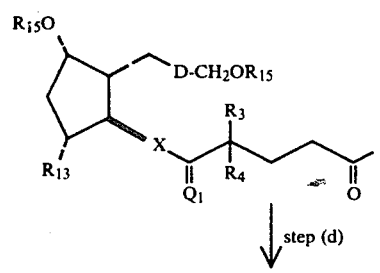
↓ step (d)
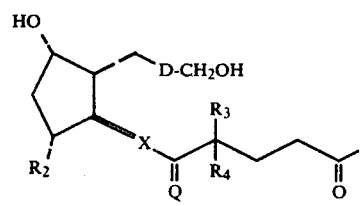
CHART 34
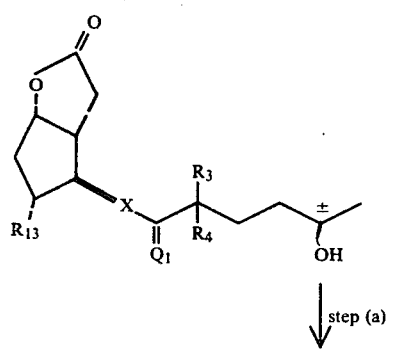
↓ step (a)
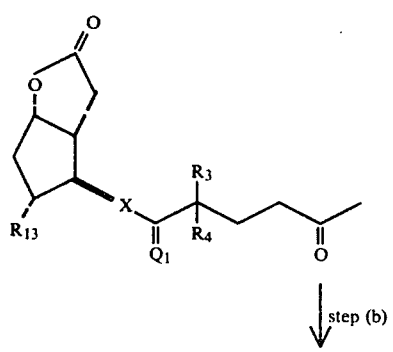
↓ step (b)
46
-continued
CHART 34
 CXCVIII
↓ step (c)
 CXCIX
↓ step (d)
 CC
↓ step (e)
 CCI
↓ step (f)
 CCII
↓ step (g)
CXCIV
CXCV
CXCVI
CXXIX
CXCVII

-continued
CHART 34
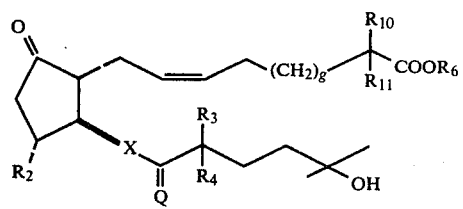
CHART 35
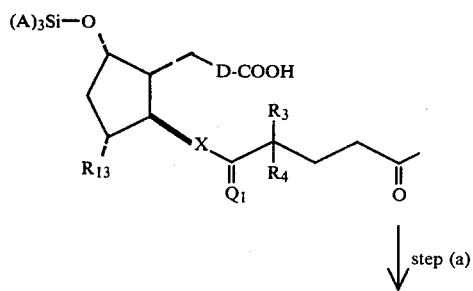
step (a)
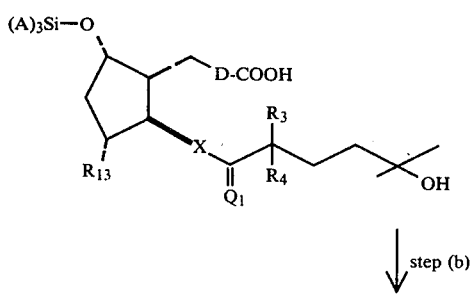
step (b)
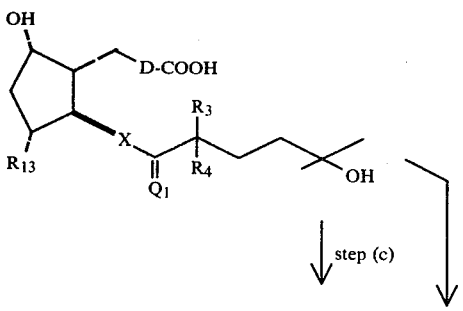
step (c)
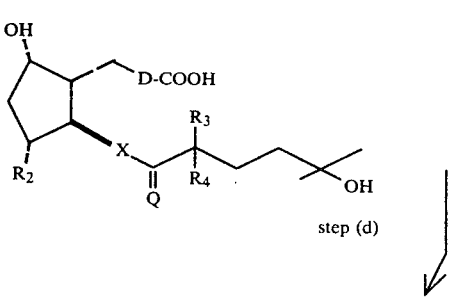
step (d)
-continued
CHART 35
CCVII
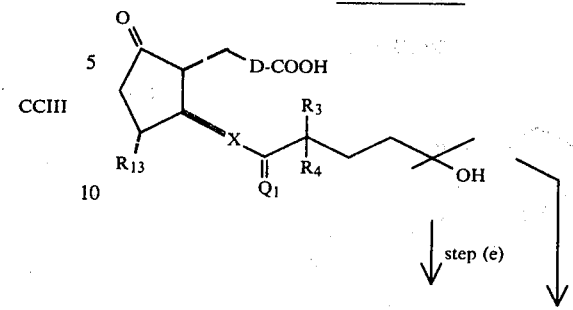
CCIII
step (e)
CCVIII
CLXXVI
CCIX
CCX
CHART 36
CCXI
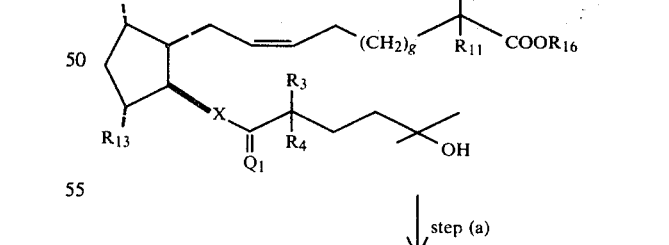
step (a)
CCVI  CCXII
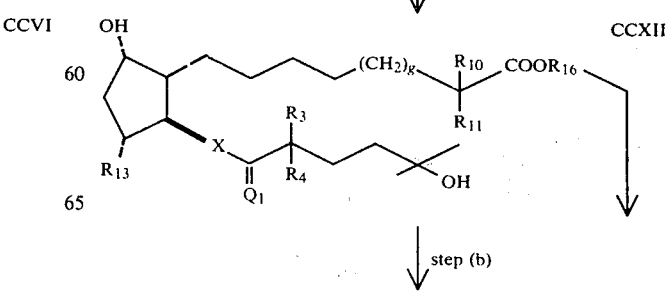
step (b)

-continued
CHART 36
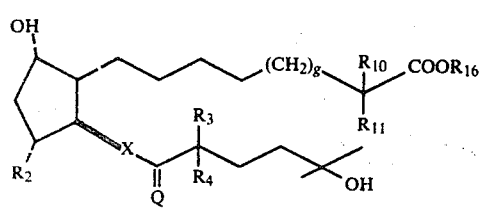 CCXIII
↓ step (c)
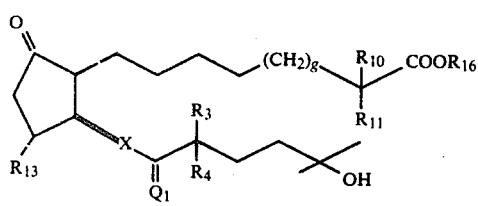 CCXIV
↓ step (d)
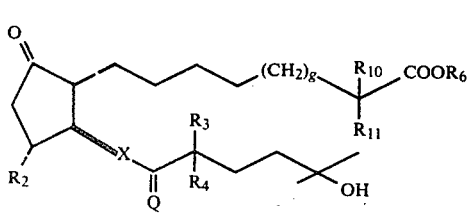 CCXV
CHART 37
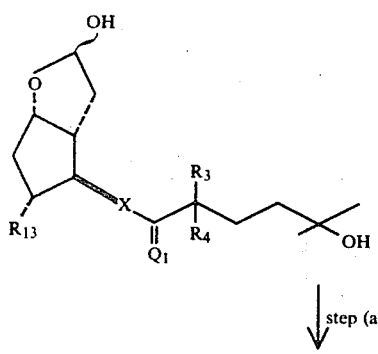 CXCIX
↓ step (a)
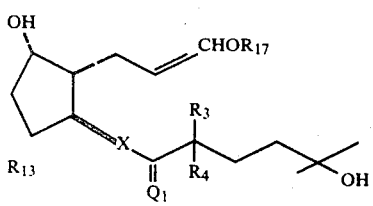 CCXVI
↓ step (b)
-continued
CHART 37
CCXVII
↓ step (c)
CCXVIII
CHART 38
CCXIX
↓ step (a)
CCXX
↓ step (b)
CCXXI
↓ step (c)
CCXXII

CHART 39

CCXXIII

CHART 40

CCXXVII

↓ step (a)

CCXXIV

↓ step (b)

CCXXVIII

↓ step (b)

CCXXV

↓ step (c)

CCXXIX

↓ step (c)

CCXXVI

↓ step (d)

CCXXX

CHART 40

CXCIX

↓ step (e)

CCXXXI

↓ step (a)

CHART 41
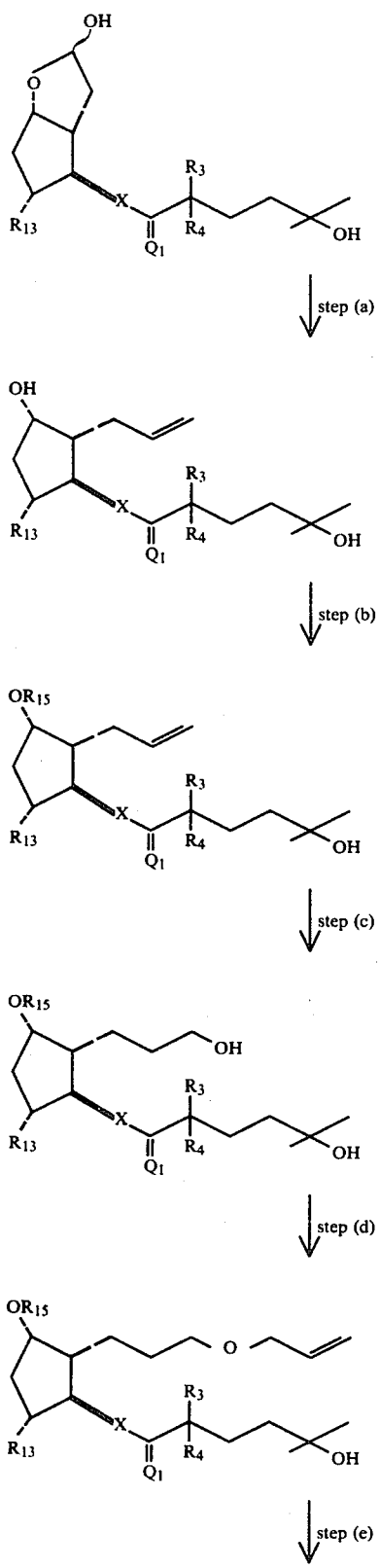
CHART 41 -continued
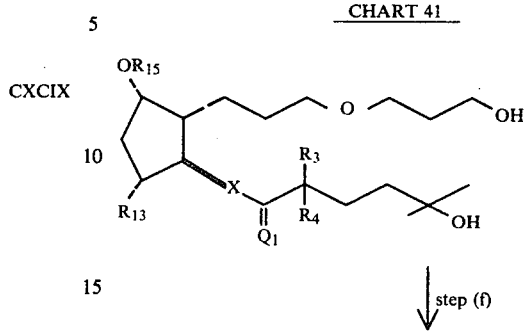
CXCIX
CCXXXVI
↓ step (f)
CCXXXVII
↓ step (g)
CCXXXVIII
CHART 42
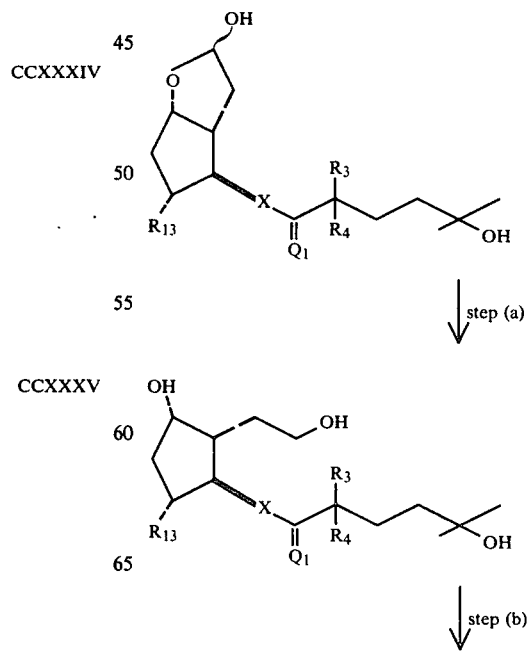
CXCIX
↓ step (a)
CCXXXIX
↓ step (b)

4,243,611
-continued
CHART 42
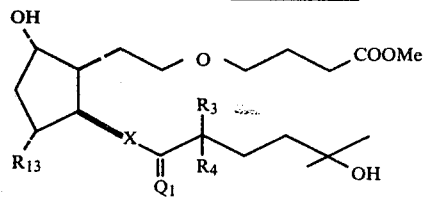
↓ step (c)
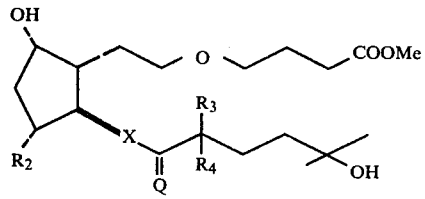
CHART 43
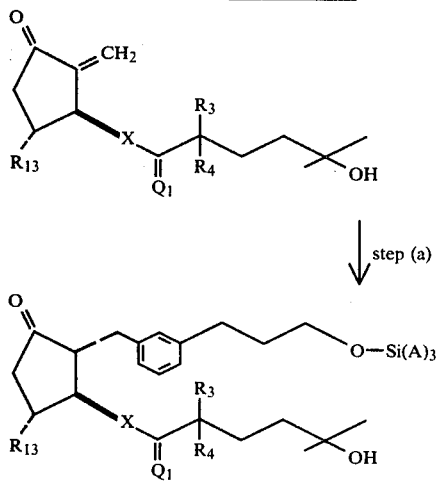
↓ step (a)
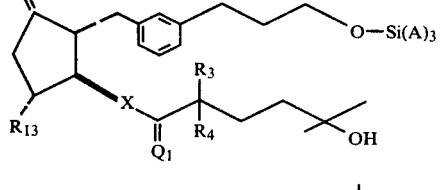
↓ step (b)
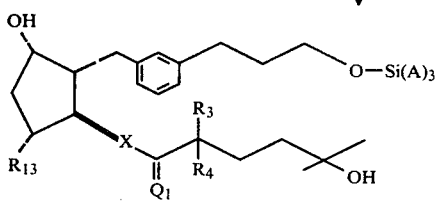
↓ step (c)
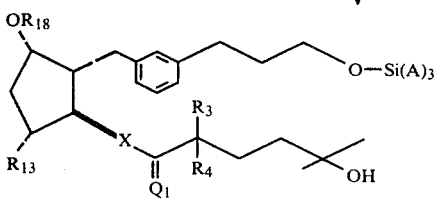
↓ step (d)
-continued
CHART 43
CCXL 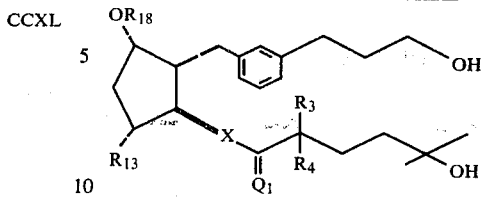 CCXLVII
↓ step (e)
CCXLI 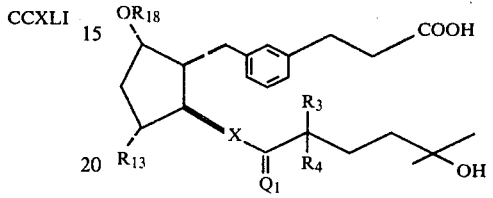 CCXLVIII
↓ step (f)
CCXLIII 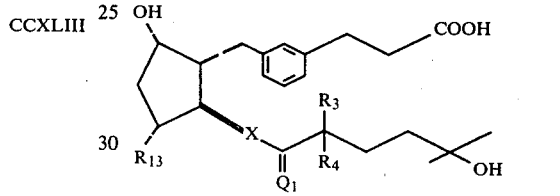 CCXLIX
↓ step (g)
CCXLIV 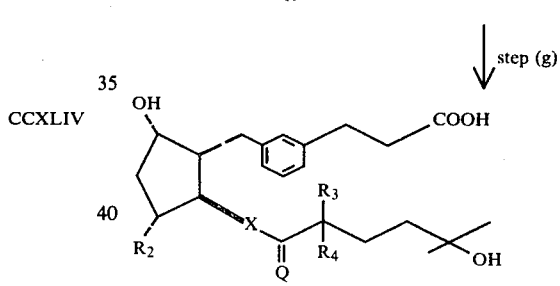 CCL
CHART 44
CCXLV 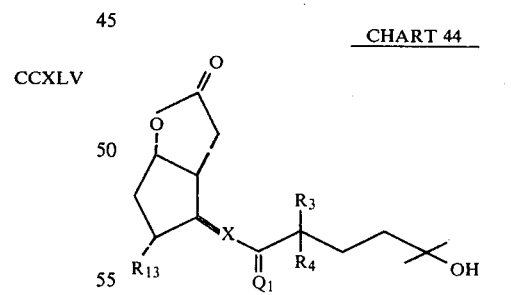 CXCVIII
↓ step (a)
CCXLVI 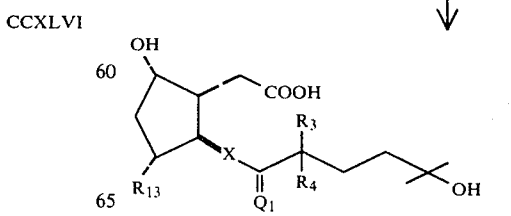 CCLI
↓ step (b)

CHART 44
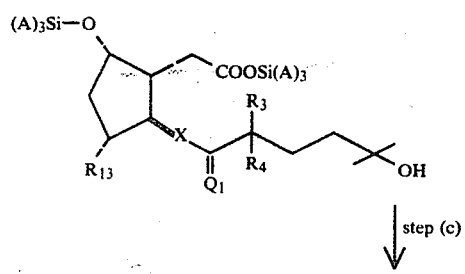
CCLII
↓ step (c)
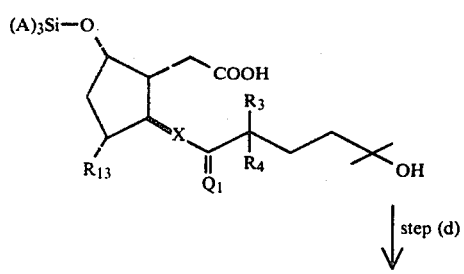
CCLIII
↓ step (d)
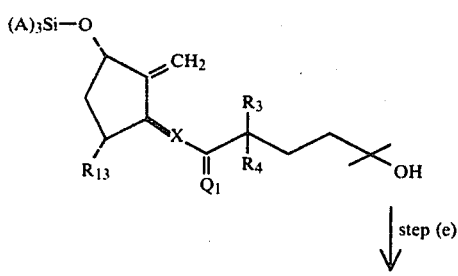
CCLIV
↓ step (e)
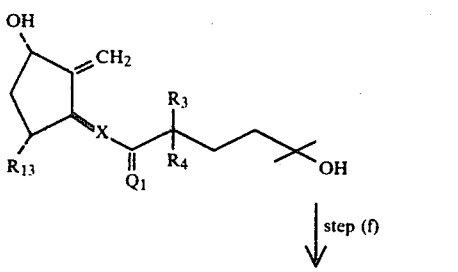
CCLV
↓ step (f)
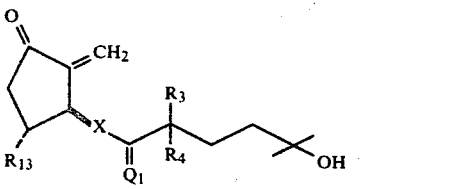
CCXLIII
CHART 45
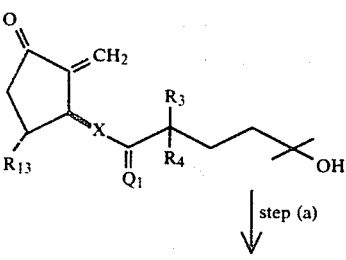
CCXLIII
↓ step (a)
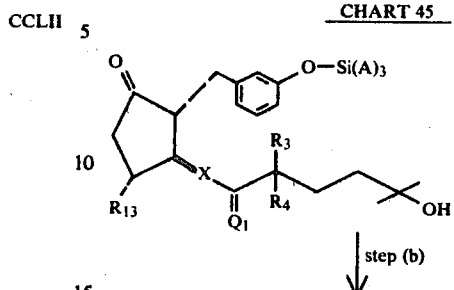
CCLVI
↓ step (b)
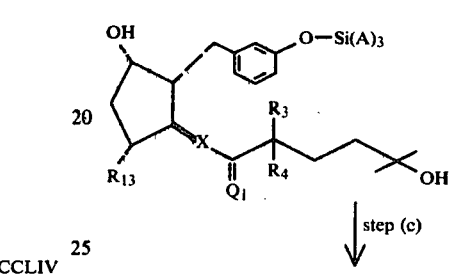
CCLVII
↓ step (c)
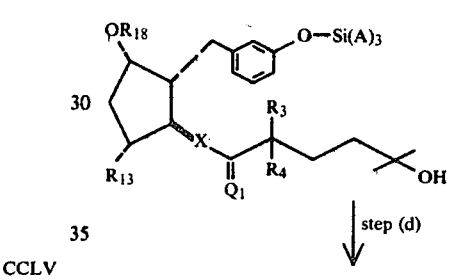
CCLVIII
↓ step (d)
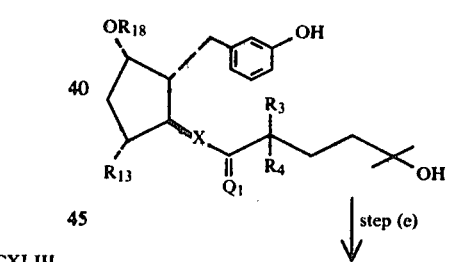
CCLIX
↓ step (e)
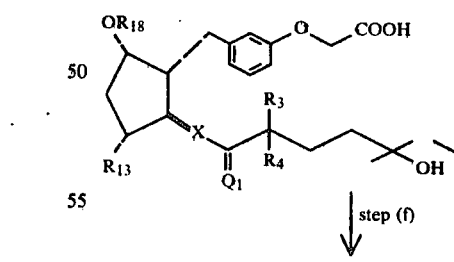
CCLX
↓ step (f)
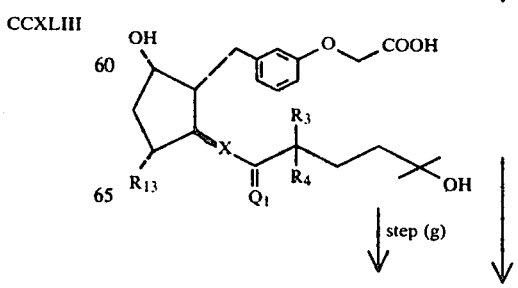
CCLXI
↓ step (g)

CHART 45 -continued
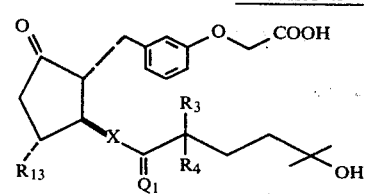 CCLXII
step (h) ↓
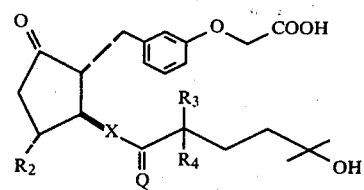 CCLXIII
step (i) ↓
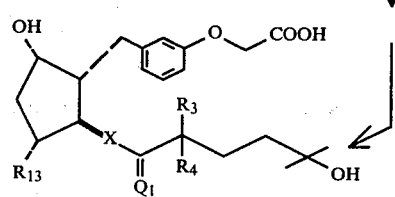 CCLXIV
step (j) ↓
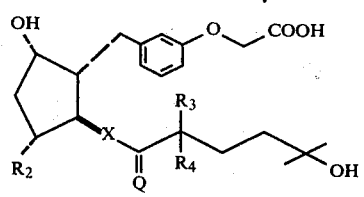 CCLXV
CHART 46
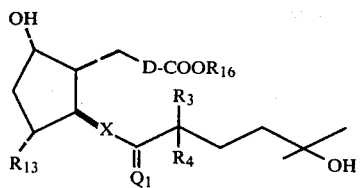 CCLXVI
step (a) ↓
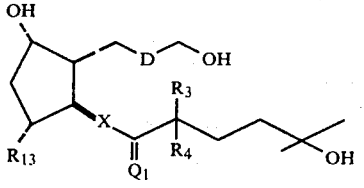 CCLXVII
step (b) ↓
CHART 46 -continued
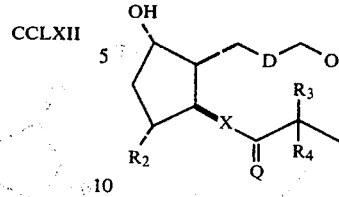 CCLXVIII
step (c) ↓
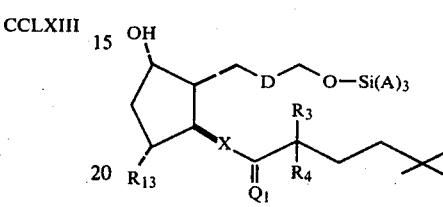 CCLXIX
step (d) ↓
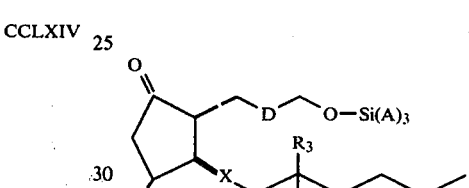 CCLXX
step (e) ↓
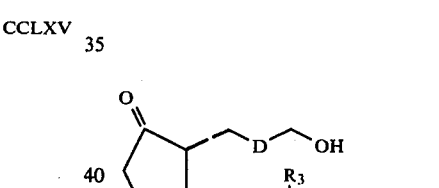 CCLXXI
CHART 47
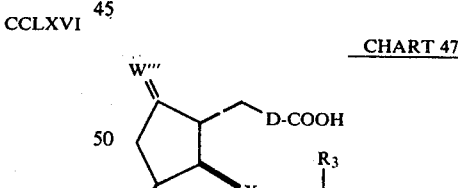 CCLXXII
step (a) ↓
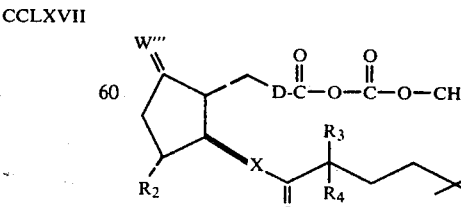 CCLXXIII
step (b) ↓

CHART 47 -continued
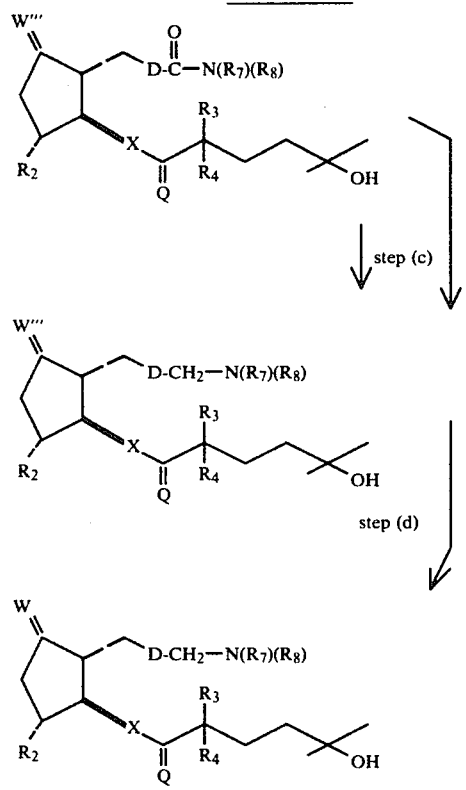
CHART 48
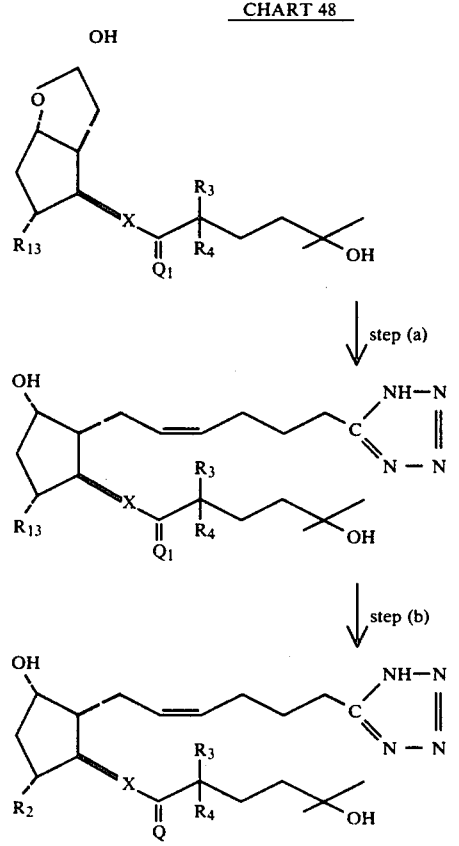
CHART 49
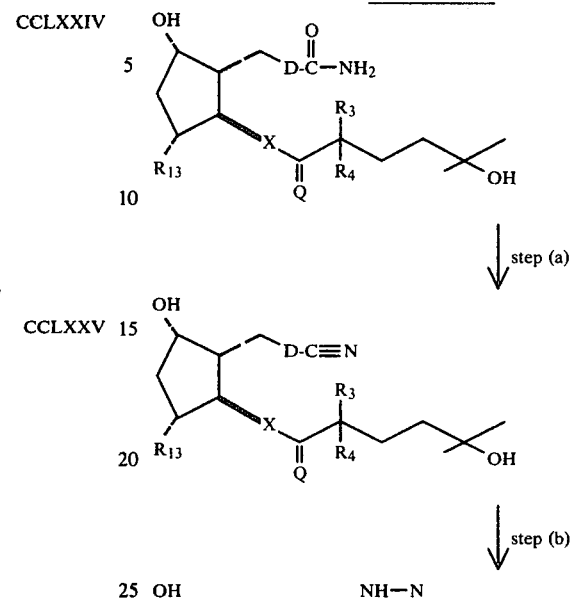
I claim:
1. A compound of the formula
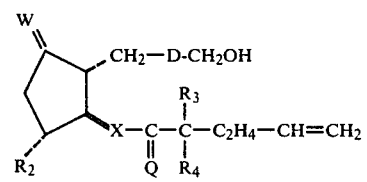
wherein D is
(1) cis—CH=CH—CH2—(CH2)g—CH2—,
(2) cis—CH=CH—CH2—(CH2)g—CF2—,
(3) cis—CH2—CH=CH—CH2—CH2—, or
(4) trans—(CH2)3—CH=CH—
wherein g is zero, one, two, or three;
wherein Q is
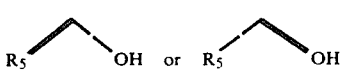
wherein $R_5$ is hydrogen or methyl, wherein W is

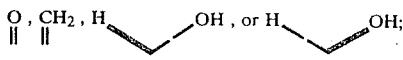

wherein X is cis- or trans—CH=CH— or —C≡C—;
wherein R₂ is hydrogen, hydroxyl, or hydroxymethyl
wherein R₃ and R₄ are hydrogen, alkyl of one to 4 carbon atoms, inclusive, or fluoro, being the same or different, with the proviso that of one R₃ and R₄ is fluoro only when the other is hydrogen or fluoro.

2. A compound according to claim 1, wherein D is cis—CH=CH—CH₂—(CH₂)ᵍ—CH₂—.

3. A compound according to claim 2, wherein W is

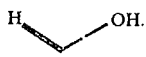

4. A compound according to claim 3, wherein R₂ is hydroxyl and X is trans—CH=CH—.

5. 2-Decarboxy-2-hydroxymethyl-19,20-didehydro-PGF₂ₐ, a compound according to claim 4.

6. A compound according to claim 3, wherein R₂ is hydrogen and X is trans—CH=CH—.

7. 2-Decarboxy-2-hydroxymethyl-11-deoxy-19,20-didehydro-PGF₂ₐ, a compound according to claim 6.

8. A compound according to claim 8, wherein R₂ is hydroxymethyl and X is trans—CH=CH—.

9. 2-Decarboxy-2-hydroxymethyl-11-deoxy-11α-hydroxy-methyl-19,20-didehydro-PGF₂ₐ, a compound according to claim 8.

10. A compound according to claim 2, wherein W is

11. A compound according to claim 10, wherein R₂ is hydroxyl and X is trans—CH=CH—.

12. 2-Decarboxy-2-hydroxymethyl-19,20-didehydro-PGF₂ᵦ, a compound according to claim 11.

13. A compound according to claim 10, wherein R₂ is hydrogen and X is trans—CH=CH—.

14. 2-Decarboxy-2-hydroxymethyl-11-deoxy-19,20-didehydro-PGF₂ᵦ, a compound according to claim 13.

15. A compound according to claim 10, wherein R₂ is hydroxymethyl and X is trans—CH=CH—.

16. 2-Decarboxy-2-hydroxymethyl-11-deoxy-11α-hydroxymethyl-19,20-didehydro-PGF₂ₐ, a compound according to claim 15.

17. A compound according to claim 2, wherein W is

18. A compound according to claim 17, wherein R₂ is hydroxyl and X is trans—CH=CH—.

19. 2-Decarboxy-2-hydroxymethyl-19,20-didehydro-PGE₂, a compound according to claim 18.

20. A compound according to claim 17, wherein R₂ is hydrogen and X is trans—CH=CH—.

21. 2-Decarboxy-2-hydroxymethyl-11-deoxy-19,20-didehydro-PGE₂, a compound according to claim 20.

22. A compound according to claim 17, wherein R₂ is hydroxymethyl and X is trans—CH=CH—.

23. 2-Decarboxy-2-hydroxymetyl-11-deoxy-11α-hydroxymethyl-19,20-didehydro-PGE₂, a compound according to claim 22.

24. A compound according to claim 2, wherein W is

25. A compound according to claim 24, wherein R₂ is hydroxyl and X is trans—CH=CH—.

26. 2-Decarboxy-2-hydroxymethyl-9-methylene-19,20-didehydro-PGE₂, a compound according to claim 25.

27. A compound according to claim 24, wherein R₂ is hydrogen and X is trans—CH=CH—.

28. 2-Decarboxy-2-hydroxymethyl-9-deoxo-9-methylene-11-deoxy-19,20-didehydro-PGE₂, a compound according to claim 27.

29. A compound according to claim 24, wherein R₂ is hydroxymethyl and X is trans—CH=CH—.

30. 2-Decarboxy-2-hydroxymethyl-9-deoxo-9-methylene-11-deoxy-11α-hydroxymethyl-19,20-didehydro-PGE₂, a compound according to claim 29.

31. A compound according to claim 1, wherein D is cis—CH₂—CH=CH—CH₂—CH₂—.

32. A compound according to claim 31, wherein W is

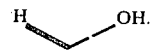

33. A compound according to claim 32, wherein R₂ is hydroxyl.

34. A compound according to claim 33, wherein X is trans—CH=CH—.

35. 2-Decarboxy-2-hydroxymethyl-4,5(4Z),19,20-tetradehydro-PGF₁ₐ, a compound according to claim 34.

36. 2-Decarboxy-2-hydroxymethyl-4,5(4Z),19,20-tetradehydro-15(S)-15-methyl-PGF₁ₐ, a compound according to claim 34.

37. A compound according to claim 33, wherein X is —C≡C—.

38. 2-Decarboxy-2-hydroxymethyl-4,5(4Z),13,14,19,20-hexahydro-PGF₁ₐ, a compound according to claim 37.

39. 2-Decarboxy-2-hydroxymethyl-4,5(4Z),13,14,19,20-hexadehydro-16,16-difluoro-PGF₁ₐ, a compound according to claim 37.

40. A compound according to claim 32, wherein R₂ is hydrogen.

41. A compound according to claim 40, wherein X is trans—CH=CH—.

42. 2-Decarboxy-2-hydroxymethyl-4,5,19,20-tetradehydro-11-deoxy-PGF₁ₐ, a compound according to claim 41.

43. 2-Decarboxy-2-hydroxymethyl-4,5(4Z),19,20-tetradehydro-11-deoxy-15(S)-15-methyl-PGF₁ₐ, a compound according to claim 41.

44. A compound according to claim 40, wherein X is —C≡C—.

45. 2-Decarboxy-2-hydroxymethyl-4,5(4Z),13,14,19,20-hexadehydro-11-deoxy-PGF₁ₐ, a compound according to claim 44.

46. 2-Decarboxy-2-hydroxymethyl-(4Z)4,5,13,14,19,20-hexadehydro-11-deoxy-16,16-difluoro-PGF₁ₐ, a compound according to claim 44.

47. A compound according to claim 32, wherein R₂ is hydroxymethyl.

48. A compound according to claim 47, wherein X is trans—CH=CH—.

49. 2-Decarboxy-2-hydroxymethyl-(4Z)4,5,19,20;-tetradehydro-11-deoxy-11α-hydroxymethyl-PGF₁α, a compound according to claim 48.

50. 2-Decarboxy-2-hydroxymethyl-(4Z)4,5,19,20-tetradehydro-11-deoxy-11α-hydroxymethyl-15(S)-15-methyl-PGF₁α, a compound according to claim 48.

51. A compound according to claim 47, wherein X is —C≡C—.

52. 2-Decarboxy-2-hydroxymethyl-(4Z)4,5,13,14,19,20-hexadehydro-11-deoxy-11α-hydroxymethyl-PGF₁α, a compound according to claim 51.

53. 2-Decarboxy-2-hydroxymethyl-(4Z)4,5,13,14,19,20-hexadehydro-11-deoxy-11α-hydroxymethyl-16,16-difluoro-PGF₁α, a compound according to claim 51.

54. A compound according to claim 31, wherein W is

55. A compound according to claim 54, wherein R₂ is hydroxyl.

56. A compound according to claim 55, wherein X is trans—CH=CH—.

57. 2-Decarboxy-2-hydroxymethyl-(4Z)4,5,19,20-tetradehydro-PGF₁β, a compound according to claim 56.

58. 2-Decarboxy-2-hydroxymethyl(4Z)4,5,19,20-tetradehydro-15(S)-15-methyl-PGF₁β, a compound according to claim 56.

59. A compound according to claim 55, wherein X is —C≡C—.

60. 2-Decarboxy-2-hydroxymethyl-(4Z)4,5,13,14,19,20-hexadehydro-PGF₁β, a compound according to claim 59.

61. 2-Decarboxy-2-hydroxymethyl-(4Z)4,5,13,14,19,20-hexadehydro-16,16-difluoro-PGF₁β, a compound according to claim 59.

62. A compound according to claim 54, wherein R₂ is hydrogen.

63. A compound according to claim 62, wherein X is trans—CH=CH—.

64. 2-Decarboxy-2-hydroxymethyl-(4Z)4,5,19,20-tetradehydro-11-deoxy-PGF₁β, a compound according to claim 63.

65. 2-Decarboxy-2-hydroxymethyl-(4Z)4,5,19,20-tetradehydro-11-deoxy-15(S)-15-methyl-PGF₁β, a compound according to claim 63.

66. A compound according to claim 62, wherein X is —C≡C—.

67. 2-Decarboxy-2-hydroxymethyl-(4Z)4,5,13,14,19,20-hexadehydro-11-deoxy-PGF₁β, a compound according to claim 66.

68. 2-Decarboxy-2-hydroxymethyl-(4Z)4,5,13,14,19,20-hexadehydro-11-deoxy-16,16-difluoro-PGF₁β, a compound according to claim 66.

69. A compound according to claim 54, wherein R₂ is hydroxymethyl.

70. A compound according to claim 69, wherein X is trans—CH=CH—.

71. 2-Decarboxy-2-hydroxymethyl-(4Z)4,5,19,20-tetradehydro-11-deoxy-11α-hydroxymethyl-PGF₁β, a compound according to claim 70.

72. 2-Decarboxy-2-hydroxymethyl-(4Z)4,5,19,20-tetradehydro-11-deoxy-11α-hydroxymethyl-15(S)-15-methyl-PGF₁β, a compound according to claim 70.

73. A compound according to claim 69, wherein X is —C≡C—.

74. 2-Decarboxy-2-hydroxymethyl-(4Z)4,5,13,14,19,20-hexadehydro-11-deoxy-11α-hydroxymethyl-PGF₁β, a compound according to claim 73.

75. 2-Decarboxy-2-hydroxymethyl-(4Z)4,5,13,14,19,20-hexadehydro-11-deoxy-11α, hydroxymethyl-16,16-difluoro-PGF₁β, a compound according to claim 73.

76. A compound according to claim 31, wherein W is $$\overset{O}{\underset{\|}{}}$$

77. A compound according to claim 76, wherein R₂ is hydroxyl.

78. A compound according to claim 77, wherein X is trans—CH=CH—.

79. 2-Decarboxy-2-hydroxymethyl-(4Z)4,5,19,20-tetradehydro-PGF₁, a compound according to claim 78.

80. 2-Decarboxy-2-hydroxymethyl-(4Z)4,5,19,20-tetradehydro-15(S)-15-methyl-PGE₁, a compound according to claim 78.

81. A compound according to claim 77, wherein X is —C≡C—.

82. 2-Decarboxy-2-hydroxymethyl-(4Z)4,5,13,14,19,20-hexadehydro-PGE₁, a compound according to claim 81.

83. 2-Decarboxy-2-hydroxymethyl(4Z)4,5,13,14,19,20-hexadehydro-16,16-difluoro-PGE₁, a compound according to claim 81.

84. A compound according to claim 76, wherein R₂ is hydrogen.

85. A compound according to claim 84, wherein X is trans—CH=CH—.

86. 2-Decarboxy-2-hydroxymethyl-(4Z)4,5,19,20-tetradehydro-11-deoxy-PGE₁, a compound according to claim 85.

87. 2-Decarboxy-2-hydroxymethyl-(4Z)4,5,19,20-tetradehydro-11-deoxy-15(S)-methyl-PGE₁, a compound according to claim 85.

88. A compound according to claim 84, wherein X is —C≡C—.

89. 2-Decarboxy-2-hydroxymethyl-(4Z)4,5,13,14,19,20-hexadehydro-11-deoxy-PGE₁, a compound according to claim 88.

90. 2-Decarboxy-2-hydroxymethyl(4Z)4,5,13,14,19,20-hexadehydro-11-deoxy-16,16-difluoro-PGE₁, a compound according to claim 88.

91. A compound according to claim 76, wherein R₂ is hydroxymethyl.

92. A compound according to claim 91, wherein X is trans—CH=CH—.

93. 2-Decarboxy-2-hydroxymethyl-(4Z)4,5,19,20-tetradehydro-11-deoxy-11α-hydroxymethyl-PGE₁, a compound according to claim 82.

94. 2-Decarboxy-2-hydroxymethyl-(4Z)4,5,19,20-tetradehydro-11-deoxy-11α-hydroxymethyl-15(S)-15-methyl-PGE₁, a compound according to claim 82.

95. A compound according to claim 91, wherein X is —C≡C—.

96. 2-Decarboxy-2-hydroxymethyl-(4Z)4,5,13,14,19,20-hexadehydro-11-deoxy-11α-hydroxymethyl-PGE₁, a compound according to claim 95.

97. 2-Decarboxy-2-hydroxymethyl-(4Z)4,5,13,14,19,20-hexadehydro-11-deoxy-11α-hydroxymethyl-16,16-difluoro-PGE₁, a compound according to claim 95.

98. A compound according to claim 31, wherein W is

99. A compound according to claim 98, wherein R₂ is hydroxyl.

100. A compound according to claim 99, wherein X is trans—CH=CH—.

101. 2-Decarboxy-2-hydroxymethyl-(4Z)4,5,19,20-tetradehydro-9-deoxo-9-methylene-PGE₁, a compound according to claim 100.

102. 2-Decarboxy-2-hydroxymethyl-(4Z)4,5,19,20-tetradehydro-9-deoxo-9-methylene-15(S)-15-methyl-PGE₁, a compound according to claim 100.

103. A compound according to claim 99, wherein X is —C≡C—.

104. 2-Decarboxy-2-hydroxymethyl-(4Z)4,5,13,14,19,20-hexadehydro-9-deoxo-9-methylene-PGE₁, a compound according to claim 103.

105. 2-Decarboxy-2-hydroxymethyl-(4Z)4,5,13,14,19,20-hexadehydro-9-deoxo-9-methylene-16,16-difluoro-PGE₁, a compound according to claim 103.

106. A compound according to claim 98, wherein R₂ is hydrogen.

107. A compound according to claim 106, wherein X is trans —CH=CH—.

108. 2-Decarboxy-2-hydroxymethyl-(4Z)4,5,19,20-tetradehydro-9-deoxo-9-methylene-11-deoxy-PGE₁, a compound according to claim 107.

109. 2-Decarboxy-2-hydroxymethyl-(4Z)4,5,19,20-tetradehydro-9-deoxo-9-methylene-11-deoxy-15(S)-15-methyl-PGE₁, a compound according to claim 107.

110. A compound according to claim 106, wherein X is —C≡C—.

111. 2-Decarboxy-2-hydroxymethyl-(4Z)4,5,13,14,19,20-hexadehydro-9-deoxy-9-methylene-11-deoxy-PGE₁, a compound according to claim 110.

112. 2-Decarboxy-2-hydroxymethyl-(4Z)4,5,13,14,19,20-hexadehydro-9-deoxo-9-methylene-11-deoxy-16,16-difluoro-PGE₁, a compound according to claim 110.

113. A compound according to claim 98, wherein R₂ is hydroxymethyl.

114. A compound according to claim 113, wherein X is trans—CH=CH—.

115. 2-Decarboxy-2-hydroxymethyl-(4Z)4,5,19,20-tetradehydro-9-deoxo-9-methylene-11-deoxy-11α-hydroxymethyl-PGE₁, a compound according to claim 114.

116. 2-Decarboxy-2-hydroxymethyl-(4Z)4,5,19,20-tetradehydro-9-deoxo-9-methylene-11-deoxy-11α-hydroxymethyl-15(S)-15-methyl-PGE₁, a compound according to claim 114.

117. A compound according to claim 113, wherein X is —C≡C—.

118. 2-Decarboxy-2-hydroxymethyl-(4Z)4,5,13,14,19,20-hexadehydro-9-deoxo-9-methylene-11-deoxy-11α-hydroxymethyl-PGE₁, a compound according to claim 117.

119. 2-Decarboxy-2-hydroxymethyl-(4Z)4,5,13,14,19,20-hexadehydro-9-deoxy-9-methylene-11-deoxy-11α-hydroxymethyl-16,16-difluoro-PGE₁, a compound according to claim 117.

120. A compound according to claim 1, wherein D is trans-(CH₂)₃—CH=CH—.

121. A compound according to claim 120, wherein W is

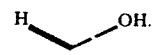

122. A compound according to claim 121, wherein R₂ is hydroxyl and X is trans—CH=CH—.

123. 2-Decarboxy-2-hydroxymethyl-2,3,(2E)19,20-tetradehydro-PGF₁α, a compound according to claim 122.

124. 2-Decarboxy-2-hydroxymethyl-2,3,(2E)19,20-tetradehydro-16,16-difluoro-PGF₁α, a compound according to claim 122.

125. 2-Decarboxy-2-hydroxymethyl-2,3,(2E)19,20-tetradehydro-15(S)-15-methyl-PGF₁α, a compound according to claim 122.

126. A compound according to claim 121, wherein R₂ is hydrogen and X is trans—CH=CH—.

127. 2-Decarboxy-2-hydroxymethyl-2,3,(2E)19,20-tetradehydro-11-deoxy-PGF₁α, a compound according to claim 126.

128. 2-Decarboxy-2-hydroxymethyl-2,3,(2E)19,20-tetradehydro-11-deoxy-16,16-difluoro-PGF₁α, a compound according to claim 126.

129. 2-Decarboxy-2-hydroxymethyl-2,3,(2E)19,20-tetradehydro-11-deoxy-15(S)-15-methyl-PGF₁α, a compound according to claim 126.

130. A compound according to claim 121, wherein R₂ is hydroxymethyl, and X is trans—CH=CH—.

131. 2-Decarboxy-2-hydroxymethyl-2,3,(2E)10,20-tetradehydro-11-deoxy-11α-hydroxymethyl-PGF₁α, a compound according to claim 130.

132. 2-Decarboxy-2-hydroxymethyl-2,3(2E)19,20-tetradehydro-11-deoxy-11α-hydroxymethyl-16,16-difluoro-PGF₁α, a compound according to claim 130.

133. 2-Decarboxy-2-hydroxymethyl-2,3,(2E)19,20-tetradehydro-11-deoxy-11α-hydroxymethyl-15(S)-15-methyl-PGF₁α, a compound according to claim 130.

134. A compound according to claim 120, wherein W is

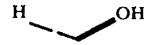

135. A compound according to claim 134, wherein R₂ is hydroxyl and X is trans—CH=CH—.

136. 2-Decarboxy-2-hydroxymethyl-2,3,(2E)19,20-tetradehydro-PGF₁β, a compound according to claim 135.

137. 2-Decarboxy-2-hydroxymethyl-2,3,(2E)19,20-tetradehydro-16,16-difluoro-PGF₁β, a compound according to claim 135.

138. 2-Decarboxy-2-hydroxymethyl-2,3,(2E)19,20-tetradehydro-15(S)-methyl-PGF$_{1\beta}$, a compound according to claim 135.

139. A compound according to claim 134, wherein R$_2$ is hydrogen and X is trans—CH=CH—.

140. 2-Decarboxy-2-hydroxymethyl-2,3,(2E)19,20-tetradehydro-11-deoxy-PGF$_{1\beta}$, a compound according to claim 139.

141. 2-Decarboxy-2-hydroxymethyll-2,3,(2E)19,20-tetradehydro-11-deoxy-16,16-difluoro-PGF$_{1\beta}$, a compound according to claim 139.

142. 2-Decarboxy-2-hydroxymethyl-2,3,(2E)19,20-tetradehydro-11-deoxy-15(S)-15-methyl-PGF$_{1\beta}$, a compound according to claim 139.

143. A compound according to claim 134, wherein R$_2$ is hydroxymethyl, and X is trans—CH=CH—.

144. 2-Decarboxy-2-hydroxymethyl-2,3,(2E)19,20-tetradehydro-11-deoxy-11α-hydroxymethyl-PGF$_{1\beta}$, a compound according to claim 143.

145. 2-Decarboxy-2-hydroxymethyl-2,3,(2E)19,20-tetradehydro-11-deoxy-11α-hydroxymethyl-16,16-difluoro-PGF$_{1\beta}$, a compound according to claim 143.

146. 2-Decarboxy-2-hydroxymethyl-2,3,(2E)19,20-tetradehydro-11-deoxy-11α-hydroxymethyl-15(S)-15-methyl-PGF$_{1\beta}$, a compound according to claim 143.

147. A compound according to claim 120, wherein W is

148. A compound according to claim 147, wherein R$_2$ is hydroxyl and X is trans—CH=CH—.

149. 2-Decarboxy-2-hydroxymethyl-2,3,(2E)19,20-tetradehydro-PGE$_1$, a compound according to claim 148.

150. 2-Decarboxy-2-hydroxymethyl-2,3,(2E)19,20-tetradehydro-16,16-difluoro-PGE$_1$, a compound according to claim 148.

151. 2-Decarboxy-2-hydroxymethyl-2,3,(2E)19,20-tetradehydro-15(S)-15-methyl-PGE$_1$, a compound according to claim 138.

152. A compound according to claim 147, wherein R$_2$ is hydrogen and X is trans—CH=CH—.

153. 2-Decarboxy-2-hydroxymethyl-2,3,(2E)19,20-tetradehydro-11-deoxy-PGE$_1$, a compound according to claim 152.

154. 2-Decarboxy-2-hydroxymethyl-2,3,(2E)19,20-tetradehydro-11-deoxy-16,16-difluoro-PGE$_1$, a compound according to claim 152.

155. 2-Decarboxy-2-hydroxymethyl-2,3,(2E)19,20-tetradehydro-11-deoxy-15(S)-15-methyl-PGE$_1$, a compound according to claim 152.

156. A compound according to claim 147, wherein R$_2$ is hydroxymethyl, and X is trans—CH=CH—.

157. 2-Decarboxy-2-hydroxymethyl-2,3,(2E)19,20-tetradehydro-11-deoxy-11α-hydroxymethyl-PGE$_1$, a compound according to claim 161.

158. 2-Decarboxy-2-hydroxymethyl-2,3,(2E)19,20-tetradehydro-11-deoxy-11α-hydroxymethyl-16,16-difluoro-PGE$_1$, a compound according to claim 161.

159. 2-Decarboxy-2-hydroxymethyl-2,3,(2E)19,20-tetradehydro-11-deoxy-11α-hydroxymethyl-15(S)-15-methyl-PGE$_1$, a compound according to claim 161.

160. A compound according to claim 120, wherein W is

161. A compound according to claim 160, wherein R$_2$ is hydroxyl and X is trans—CH=CH—.

162. 2-Decarboxy-2-hydroxymethyl-2,3,(2E)19,20-tetradehydro-9-deoxo-9-methylene-PGE$_1$, a compound according to claim 161.

163. 2-Decarboxy-2-hydroxymethyl-2,3,(2E)19,20-tetradehydro-9-deoxo-9-methylene-16,16-difluoro-PGE$_1$, a compound according to claim 161.

164. 2-Decarboxy-2-hydroxymethyl-2,3,(2E)19,20-tetradehydro-9-deoxo-9-methylene-15(S)-15-methyl-PGE$_1$, a compound according to claim 161.

165. A compound according to claim 160, wherein R$_2$ is hydrogen and X is trans—CH=CH—.

166. 2-Decarboxy-2-hydroxymethyl-2,3,(2E)19,20-tetradehydro-9-deoxo-9-methylene-11-deoxy-PGE$_1$, a compound according to claim 170.

167. 2-Decarboxy-2-hydroxymethyl-2,3,(2E)19,20-tetradehydro-9-deoxo-9-methylene-11-deoxy-16,16-difluoro-PGE$_1$, a compound according to claim 165.

168. 2-Decarboxy-2-hydroxymethyl-2,3,(2E)19,20-tetradehydro-9-deoxo-9-methylene-11-deoxy-15(S)-15-methyl-PGE$_1$, a compound according to claim 165.

169. A compound according to claim 160, wherein R$_2$ is hydroxymethyl, and X is trans—CH=CH—.

170. 2-Decarboxy-2-hydroxymethyl-2,3,(2E)19,20-tetradehydro-9-deoxo-9-methylene-11-deoxy-11α-hydroxymethyl-PGE$_1$, a compound according to claim 169.

171. 2-Decarboxy-2-hydroxymethyl-2,3,(2E)19,20-tetradehydro-9-deoxo-9-methylene-11-deoxy-11α-hydroxymethyl-16,16-difluoro-PGE$_1$, a compound according to claim 169.

172. 2-Decarboxy-2-hydroxymethyl-2,3,(2E)19,20-tetradehydro-9-deoxo-9-methylene-11-deoxy-11α-hydroxymethyl-15-(S)-15-methyl-PGE$_1$, a compound according to claim 169.

* * * * *

UNITED STATES PATENT OFFICE
CERTIFICATE OF CORRECTION

Patent No. 4,243,611                      Dated 6 January 1981

Inventor(s) John C. Sih

It is certified that error appears in the above-identified patent and that said Letters Patent are hereby corrected as shown below:

In the Abstract, the formula appearing therein should read as follows:

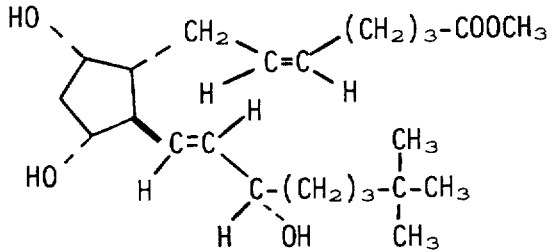

Column 63, line 28, "according to claim 8" should read -- according to claim 3 --;

Column 64, line 55, "4,5,19,20-tetradehydro-" should read -- 4,5,(4Z)-19,20-tetradehydro- --;

Column 68, line 45, "2,3,(2E)10,20-tetradehydro-" should read -- 2,3,(2E)19,20-tetradehydro- --;

Column 69, line 43, "according to claim 138" should read -- according to claim 148 --;

Column 70, line 34, "according to claim 170" should read -- according to claim 165 --.

Signed and Sealed this

Ninth Day of November 1982

[SEAL]

Attest:

Attesting Officer

GERALD J. MOSSINGHOFF
Commissioner of Patents and Trademarks